(12) United States Patent
Foley et al.

(10) Patent No.: US 10,118,018 B2
(45) Date of Patent: Nov. 6, 2018

(54) URINARY CATHETER DEPLOYMENT CASSETTES

(71) Applicant: Hollister Incorporated, Libertyville, IL (US)

(72) Inventors: Adam J. Foley, Swords (IE); Michael G. Murray, Ballina (IE); Iarla Marron, Raheny (IE); Patrick E. O'Dowd, Dunsany (IE)

(73) Assignee: HOLLISTER INCORPORATED, Libertyville, IL (US)

( * ) Notice: Subject to any disclaimer, the term of this patent is extended or adjusted under 35 U.S.C. 154(b) by 342 days.

(21) Appl. No.: 14/899,252

(22) PCT Filed: Jul. 22, 2014

(86) PCT No.: PCT/US2014/047565
§ 371 (c)(1),
(2) Date: Dec. 17, 2015

(87) PCT Pub. No.: WO2015/013251
PCT Pub. Date: Jan. 29, 2015

(65) Prior Publication Data
US 2016/0136391 A1  May 19, 2016

Related U.S. Application Data

(60) Provisional application No. 61/857,282, filed on Jul. 23, 2013.

(51) Int. Cl.
*A61M 25/01* (2006.01)
*A61M 25/08* (2006.01)
*A61M 25/00* (2006.01)

(52) U.S. Cl.
CPC ....... *A61M 25/0111* (2013.01); *A61M 25/002* (2013.01); *A61M 25/0113* (2013.01); *A61M 25/0017* (2013.01)

(58) Field of Classification Search
CPC ............ A61M 25/0111; A61M 25/002; A61M 25/0113; A61M 25/0017;
(Continued)

(56) References Cited

U.S. PATENT DOCUMENTS 3,545,608 A   12/1970  Bertger et al.
3,565,144 A    2/1971  Annenmans
(Continued)

FOREIGN PATENT DOCUMENTS

EP     0800 413 B1   10/1997
SU       818608       7/1981
(Continued)

OTHER PUBLICATIONS

International Search Report ancf Written Opinion for PCT/US2014/047565, dated Oct. 8, 2014.

*Primary Examiner* — Adam Marcetich
(74) *Attorney, Agent, or Firm* — Cook Alex Ltd.

(57) ABSTRACT

A urinary catheter deployment cassette or system includes a catheter pack, a urinary catheter, and an introducer aid. The catheter pack defines an interior compartment having a rotatable spindle at least partially positioned therein. The urinary catheter is at least partially received within the interior compartment of the catheter pack and associated with the spindle. The catheter pack includes a deformable or pierceable cover that the spindle engagement member of the introducer aid is pressed to rotate the spindle and deploy the catheter from the catheter pack. In another embodiment, a catheter pack includes an associated drainage adaptor for draining fluid from the catheter pack or a urinary catheter positioned within the catheter pack. In another embodiment, a cassette includes a rotatable drum with a two-piece catheter wrapped around it and a joining tube that places the pieces of the catheter in fluid communication.

20 Claims, 27 Drawing Sheets

(58) Field of Classification Search
CPC ............ A61M 25/09041; A61M 5/002; B65H 75/4471; B65H 54/585; B65H 75/40; B65H 75/02; B60P 7/0823; B60P 7/083; B60P 7/0838; B60P 7/0846; B60P 7/0853; B60P 7/0861; B60P 7/0869; H02G 11/02

See application file for complete search history.

(56) References Cited

U.S. PATENT DOCUMENTS

| | | | | |
|---|---|---|---|---|
| 3,749,238 | A * | 7/1973 | Taylor | A61B 17/06123 206/227 |
| 3,995,628 | A | 12/1976 | Gula et al. | |
| 4,130,122 | A * | 12/1978 | Kennedy | A45D 6/04 132/238 |
| 4,397,091 | A | 8/1983 | Gustavsson et al. | |
| 4,479,762 | A | 10/1984 | Bilstad et al. | |
| 4,692,034 | A | 9/1987 | Fukui et al. | |
| 4,713,059 | A | 12/1987 | Bickelhaupt et al. | |
| 4,721,123 | A | 1/1988 | Cosentino et al. | |
| 4,858,821 | A | 8/1989 | Bickelhaupt | |
| 5,392,808 | A | 2/1995 | Pierce | |
| 5,526,928 | A | 6/1996 | Yabe et al. | |
| 5,542,539 | A | 8/1996 | Early | |
| 5,590,778 | A | 1/1997 | Dutchik | |
| 5,855,567 | A | 1/1999 | Reesermann | |
| 6,631,866 | B1 * | 10/2003 | Obrink | A01K 89/016 242/390.8 |
| 6,896,141 | B2 | 5/2005 | McMichael et al. | |
| 7,678,088 | B2 | 3/2010 | Egle et al. | |
| 7,766,162 | B2 | 8/2010 | Maki et al. | |
| 2002/0195143 | A1 * | 12/2002 | Paplow | B65H 75/40 137/355.2 |
| 2003/0077414 | A1 * | 4/2003 | Clark | G09F 3/02 428/64.1 |
| 2003/0098067 | A1 * | 5/2003 | Peterson | A61M 16/08 137/355.2 |
| 2004/0250951 | A1 * | 12/2004 | Noworatzky | B65C 3/02 156/277 |
| 2006/0035770 | A1 * | 2/2006 | Crowson | A63B 21/00 482/129 |
| 2006/0180800 | A1 * | 8/2006 | Tremblay | B60P 7/083 254/229 |
| 2007/0001050 | A1 * | 1/2007 | Taatjes | B65H 49/322 242/598.6 |
| 2007/0045460 | A1 * | 3/2007 | Cupan | B60P 7/0846 242/388.1 |
| 2009/0071851 | A1 * | 3/2009 | Maki | A61M 25/002 206/210 |
| 2009/0236458 | A1 * | 9/2009 | Rodrique | B60P 7/0846 242/374 |
| 2010/0039914 | A1 * | 2/2010 | Yao | G11B 7/00736 369/53.21 |
| 2010/0130923 | A1 | 5/2010 | Cleary et al. | |
| 2011/0312232 | A1 * | 12/2011 | Starck, Jr. | B63B 35/7933 441/75 |
| 2013/0006226 | A1 * | 1/2013 | Hong | A61M 25/0017 604/544 |
| 2013/0167960 | A1 * | 7/2013 | Pethe | F17C 13/00 137/798 |
| 2013/0178836 | A1 * | 7/2013 | Teutsch | A61M 39/08 604/533 |
| 2013/0345681 | A1 | 12/2013 | Hong et al. | |

FOREIGN PATENT DOCUMENTS

| | | |
|---|---|---|
| WO | WO 01/78824 | 10/2001 |
| WO | WO 2012/166967 | 6/2012 |

* cited by examiner

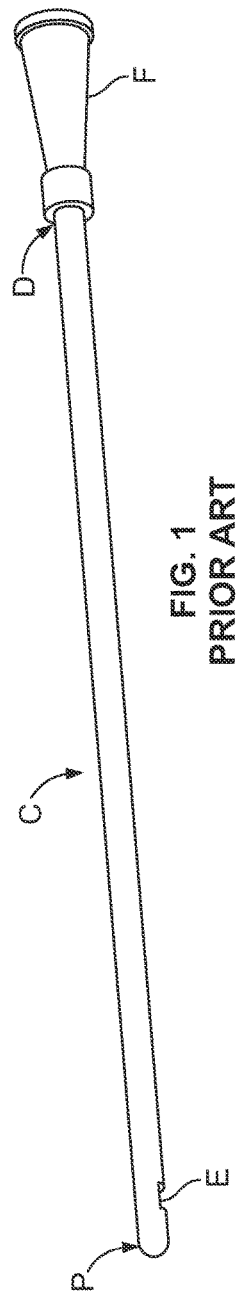
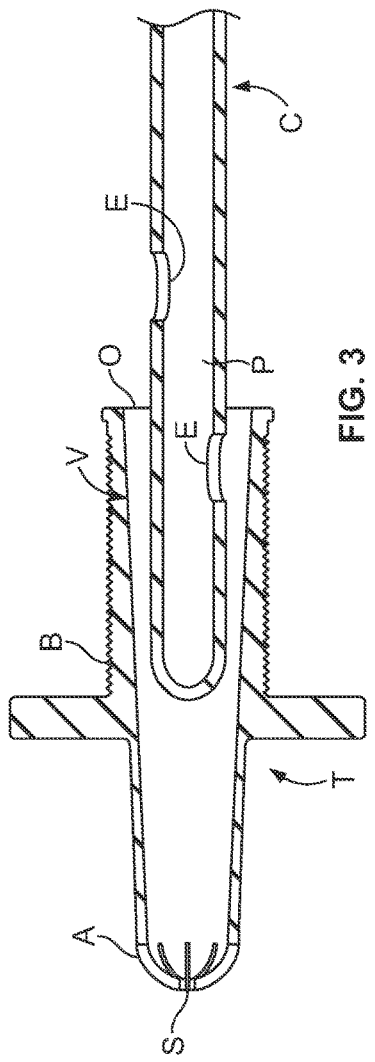
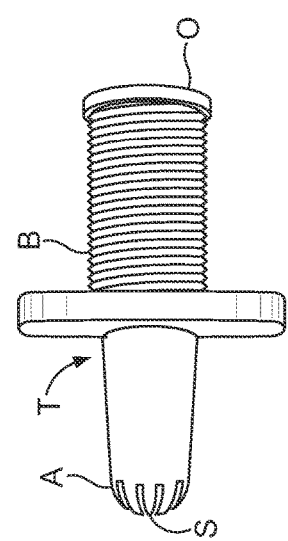
FIG. 1
PRIOR ART
FIG. 2
PRIOR ART
FIG. 3
PRIOR ART

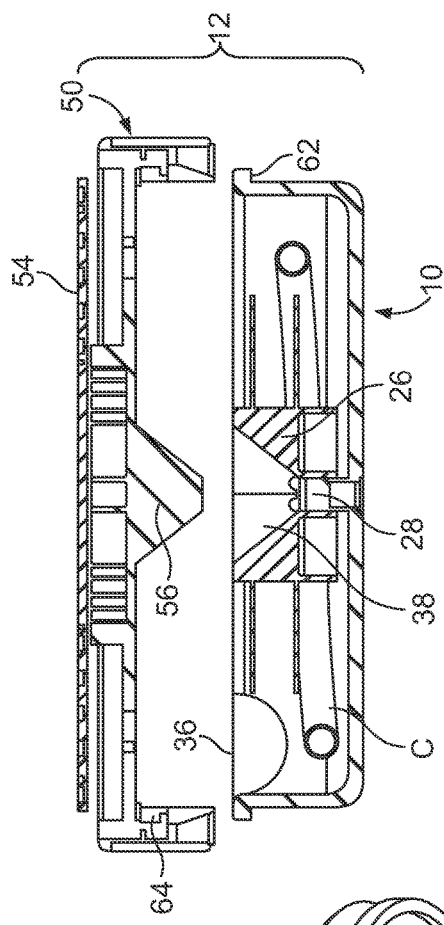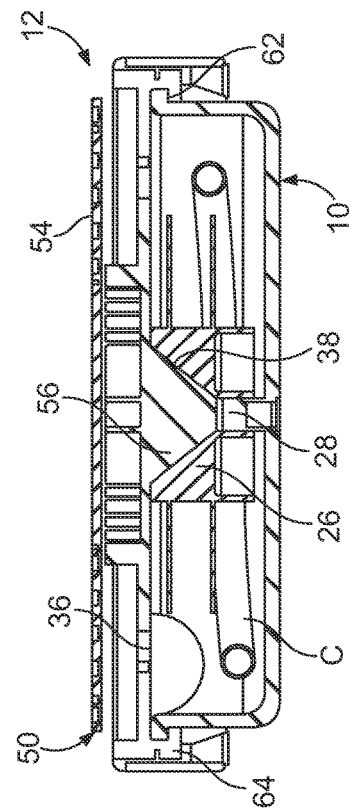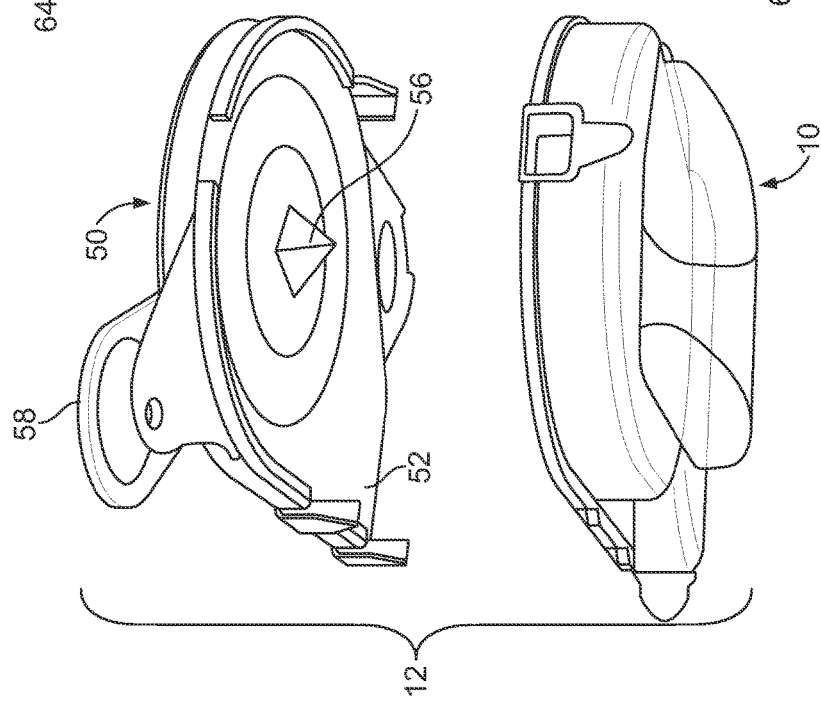
FIG. 20
FIG. 21
FIG. 19

US 10,118,018 B2

URINARY CATHETER DEPLOYMENT CASSETTES

RELATED APPLICATION

This application is a U.S. national stage application of PCT Patent Application Serial No. PCT/US2014/047565, filed Jul. 22, 2014, which claims the benefit of and priority of U.S. Provisional Patent Application Ser. No. 61/857,282, filed Jul. 23, 2013, the contents of both of which are incorporated herein by reference.

DESCRIPTION

Technical Field

The present disclosure generally relates to urinary catheters. More particularly, the present disclosure relates to cassettes for deploying urinary catheters.

Background

Catheters are used to treat many different types of medical conditions and typically include an elongated shaft that is inserted into and through a passageway or lumen of the body. Catheters, and in particular intermittent catheters, are commonly used by those who suffer from various abnormalities of the urinary system, such as urinary incontinence. With the advent of intermittent catheters, individuals with urinary system abnormalities can self-insert and self-remove intermittent catheters several times a day. Such catheters typically include a shaft that is sufficiently flexible to navigate the curves of the urethra (especially catheters intended for male users), yet rigid enough to be pushed through the urethra without collapsing or buckling before an end of the catheter reaches the bladder.

With proper training and experience, urinary catheters may be easily used by those of sufficient hand dexterity. However, for those of limited hand dexterity, using a urinary catheter can be difficult, such that it would be advantageous to provide a urinary catheter deployment system for users of limited hand dexterity.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a urinary catheter deployment system is provided. The system includes a catheter pack, a urinary catheter, and an introducer aid. The catheter pack defines an interior compartment having a rotatable spindle at least partially positioned therein. A deformable or pierceable cover is associated with the interior compartment. The urinary catheter is at least partially positioned within the interior compartment of the catheter pack and associated with the spindle. The introducer aid includes at least one spindle engagement member configured to cooperate with the catheter pack to deform or pierce the cover and engage the spindle for deploying the urinary catheter from the catheter pack.

In another aspect, a urinary catheter deployment system is provided. The system includes a catheter pack, a urinary catheter, and a pusher. The catheter pack defines an interior compartment having a rotatable spindle, the urinary catheter, and the pusher at least partially positioned therein. The pusher is associated with the spindle and configured to rotate therewith and contact the urinary catheter, thereby deploying the urinary catheter from the catheter pack.

In yet another aspect, a urinary catheter deployment system is provided. The system includes a housing, with a rotatable inner drum and urinary catheter at least partially positioned within an interior compartment of the housing. The urinary catheter is associated with the inner drum such that rotation of the inner drum deploys the urinary catheter from the housing. The urinary catheter includes separate first and second pieces that are secured to the inner drum, with the inner drum having a joining tube in fluid communication with the two pieces of the urinary catheter.

BRIEF DESCRIPTION OF THE DRAWINGS

FIG. 1 is a perspective view of a male urinary catheter according to a known design;

FIG. 2 is a side elevational view of a protective tip according to a known design for use in combination with the catheter of FIG. 1;

FIG. 3 is a cross-sectional view of the catheter of FIG. 1 partially positioned within the protective tip of FIG. 2;

FIG. 19 is a bottom perspective view of the catheter pack of FIGS. 4-15 being moved into engagement with the introducer aid of FIGS. 16-18;

FIG. 20 is a cross-sectional view of the catheter pack of FIGS. 4-15 being moved into engagement with the introducer aid of FIGS. 16-18;

FIG. 21 is a cross-sectional view of the catheter pack of FIGS. 4-15 in cooperative engagement with the introducer aid of FIGS. 16-18 to define a deployment cassette or system;

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

An exemplary male urinary catheter C according to conventional design is shown in FIG. 1. A proximal end P of the catheter C includes one or more draining holes or eyes E for the drainage of bodily fluids therethrough and into an internal conduit or lumen of the catheter C. The distal end D of the catheter may include a connecting member F, such as a funnel, for fluidly connecting the catheter C to a collection container, such as a collection bag into which urine drains.

The catheter C may be used in combination with a protective tip or cover T (FIG. 2) that substantially encircles at least a portion of the proximal end P. FIG. 3 shows the proximal end P of the catheter C received within the protective tip T. The protective tip T has a generally tubular body portion B defining an interior cavity V (FIG. 3) that extends between an open end O and an access end A. The open end O is the end of the protective tip T into which the catheter C is inserted (in a direction toward the access end A). The access end A is movable between a generally closed condition when the proximal end P of the catheter C is positioned within the protective tip T (illustrated) and a generally open condition when the catheter C is advanced proximally (i.e., in a right-to-left direction in the orientation of FIG. 3) so as to pass through the access end A for advancement into and through the urethra. As shown in FIGS. 2 and 3, the access end A of the protective tip T may include one or more slits S, according to conventional design, that allow it to move between the generally closed and generally open conditions.

The protective tip T serves to isolate the proximal end P of the catheter C (including the eyes E) from the outside environment (e.g., from touch contamination whereby bacteria present on a user's hands might be transferred to the proximal end P of the catheter C) prior to insertion into the urethra and from the relatively high concentration of bacteria typically present in the distal urethra. By isolating the proximal end P of the catheter C from the outside environment, the sterility of the proximal end P may be maintained.

Figure 4:
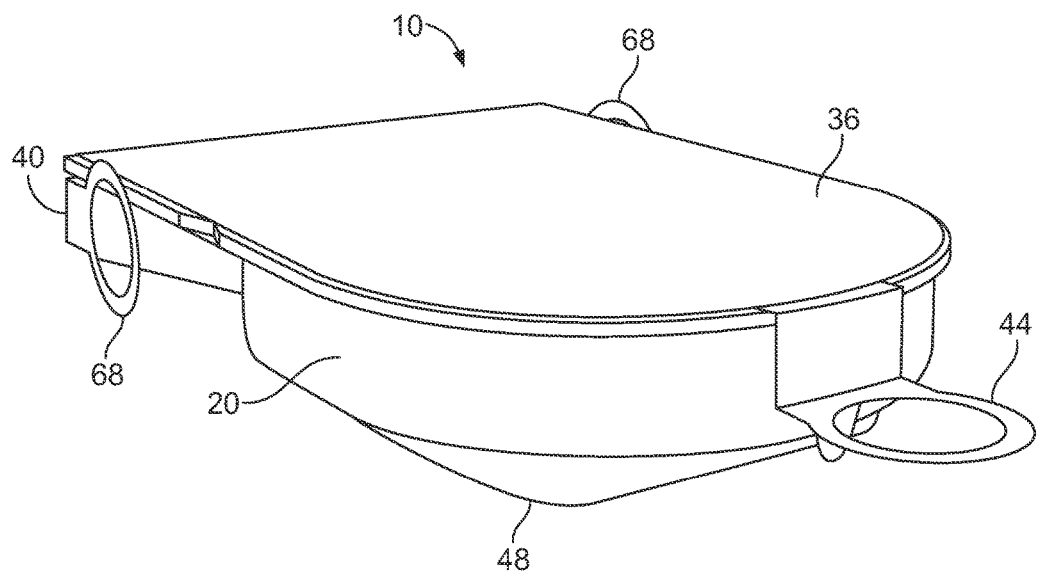
FIG. 4 is a perspective view of a packaged catheter pack of a urinary catheter deployment system or cassette according to an aspect of the present disclosure.
Figure 5:
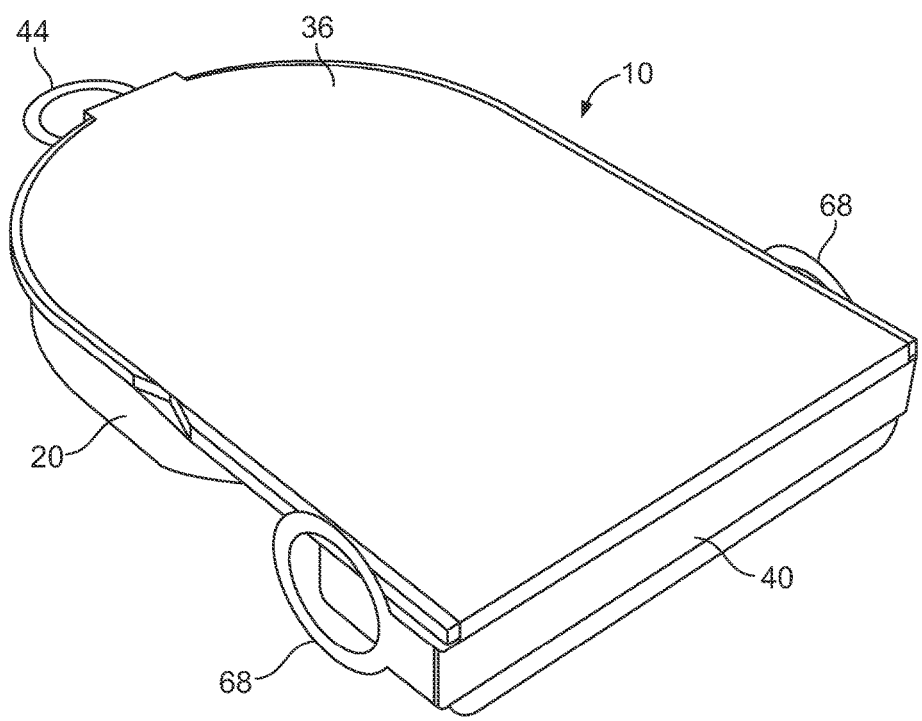
FIG. 5 is a rear perspective view of the packaged catheter pack of FIG. 4.
Figure 6:
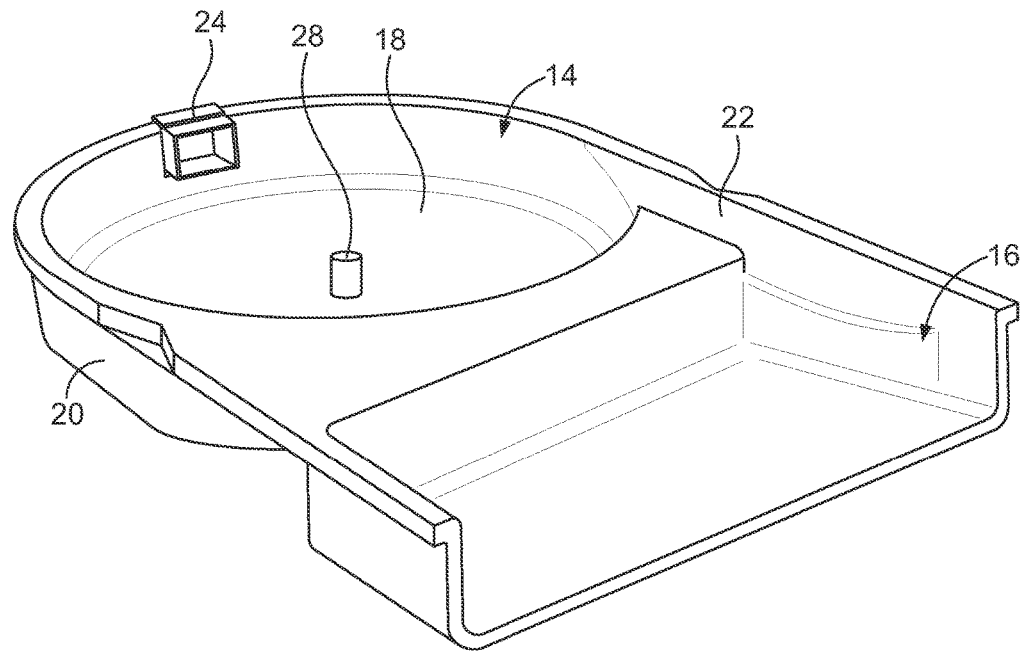
FIG. 6 is a perspective view of the housing or body of the catheter pack of FIG. 4.
Figure 7:
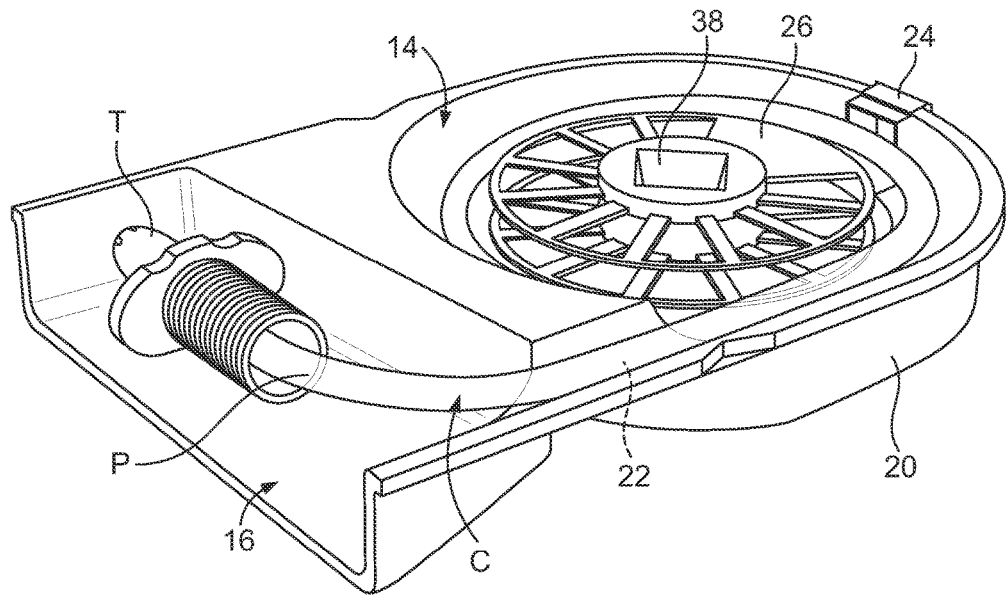
FIG. 7 is a perspective view of the catheter pack housing or body of FIG. 6, with a spindle and catheter positioned within the housing or body.
Figure 8:
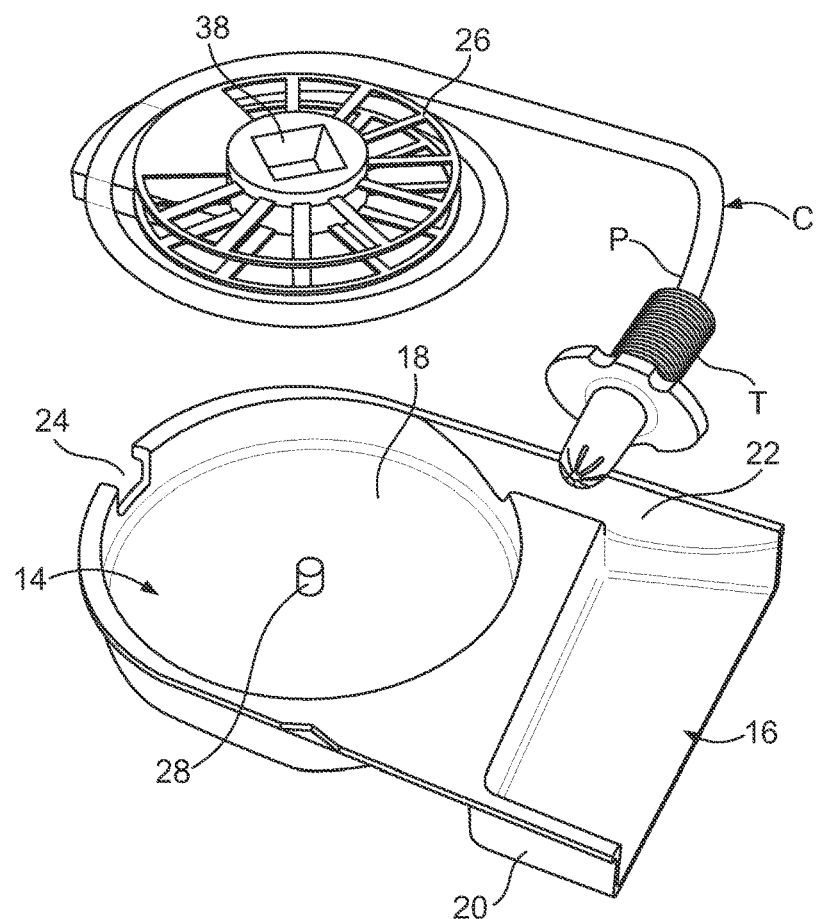
FIG. 8 is an exploded view of the catheter pack housing or body, spindle, and catheter of FIG. 7.

FIGS. 4-15 show one embodiment of a catheter pack or package 10 of a deployment cassette or system 12 (FIG. 19). As seen in FIGS. 6-8, the catheter pack 10 may define an interior chamber or compartment 14 in which at least a portion of a catheter C may be received. In the illustrated embodiment, only a portion of the catheter C is positioned and housed within the interior compartment 14, with the proximal end P of the catheter C, including the protective tip T being positioned and housed within an adjacent, adjoining interior compartment 16 of the catheter pack 10. In a preferred embodiment, the catheter C is provided without a funnel F at its distal end D, but it is also within the scope of the present disclosure for the catheter C to include a distal funnel F or the like without departing from the scope of the present disclosure.

The illustrated first interior compartment 14 is defined by a bottom wall 18 and upstanding sidewall 20 to have a generally circular or cylindrical shape, with a passage 22 extending through the sidewall 20 to allow the first interior compartment 14 to communicate with the second interior compartment 16. The sidewall 20 includes a drainage opening or passage 24 that allows communication between the first interior compartment 14 and the outside of the catheter pack 10. The drainage opening 24 allows for removal of urine or fluid from the catheter pack 10, as will be described in greater detail herein.

FIG. 7 shows a catheter C positioned within the catheter pack 10, with a distal portion of the catheter C wrapped around a spool or spindle 26 located within the first interior compartment 14. The spindle 26 and catheter C are further illustrated in FIGS. 8-11. At least a portion of the spindle 26 is configured to rotate within the first interior compartment 14, such as by rotating about a pin or peg 28 extending into the compartment 14 from the bottom wall 18. In one embodiment, only an upper portion of the spindle 26 (i.e., the portion spaced away from the bottom wall 18) rotates, while a lower portion of the spindle 26 does not rotate, but is instead substantially stationary with respect to the catheter pack 10. In such an embodiment, the pin or peg 28 (if provided) may be used to properly position the spindle 26 within the interior compartment 14 without the spindle 26 rotating about the pin or peg 28. At least a portion of the spindle 26 rotates to advance or pay out the catheter C from the interior compartment 14, via the passage 22 and the second interior compartment 16, as seen in FIG. 10 and as will be described in greater detail.

Figure 9:
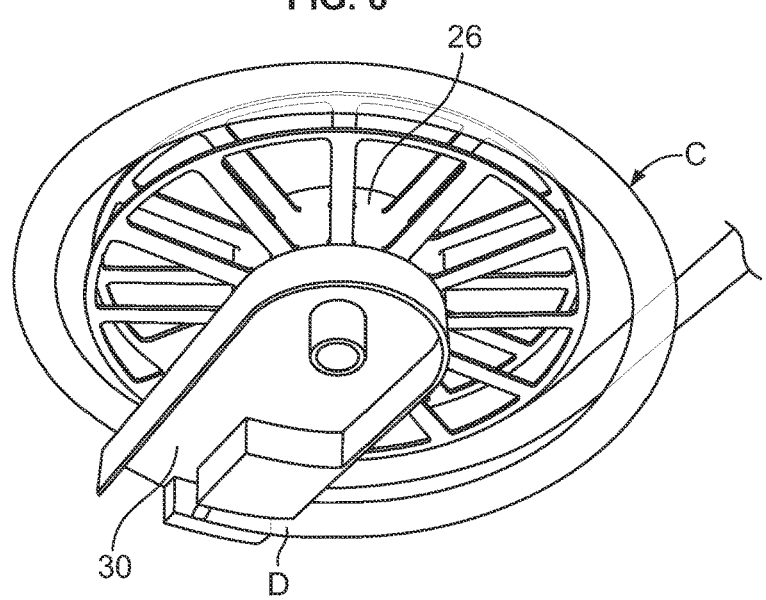
FIG. 9 is a bottom perspective view of the spindle and catheter of FIG. 7.
Figure 10:
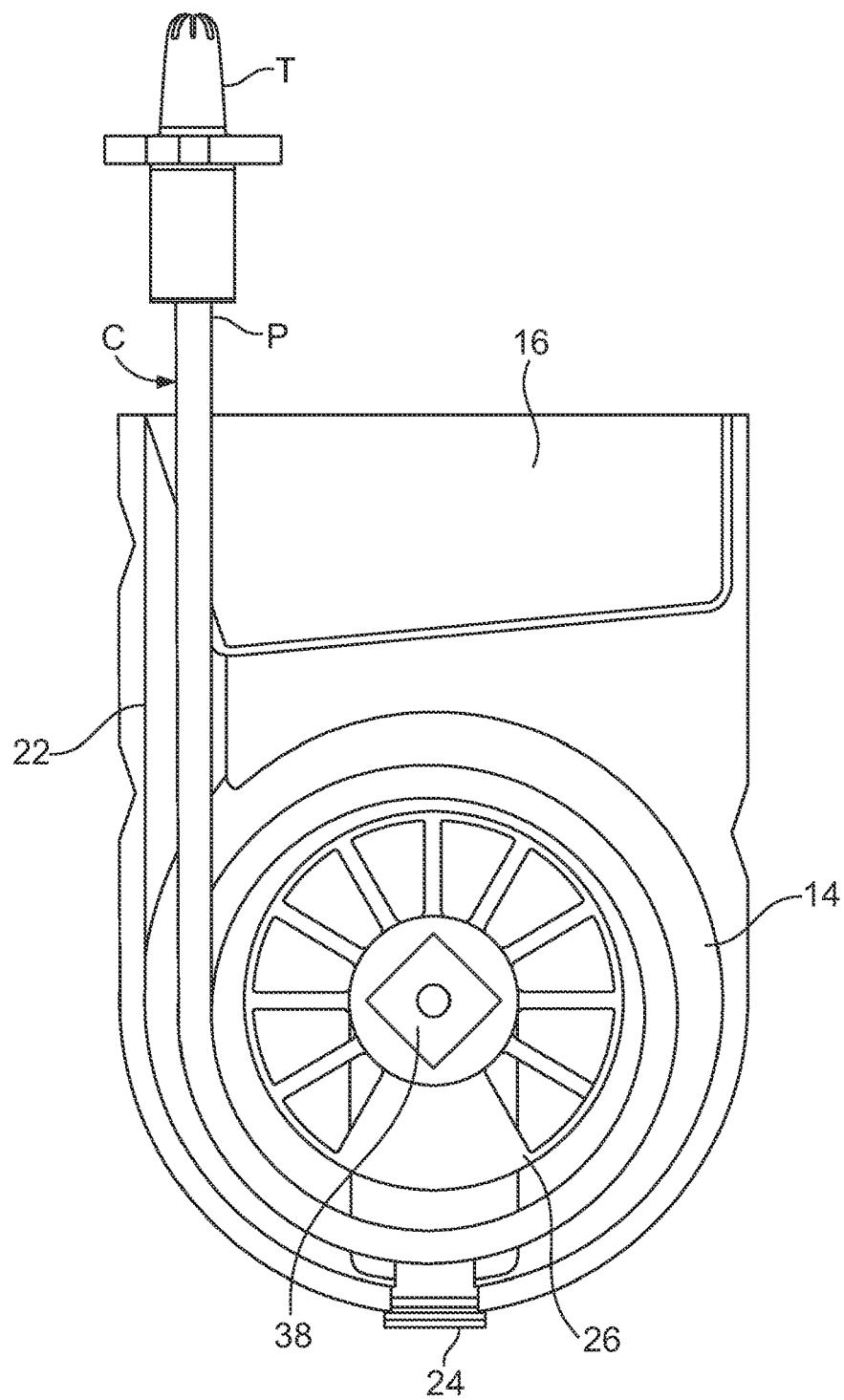
FIG. 10 is a top plan view of the catheter pack housing or body, spindle, and catheter of FIG. 7.

As best shown in FIG. 9, the distal end D of the catheter C may be connected or secured to a portion of the spindle 26. If the distal end D of the catheter C is secured or connected to the spindle 26, it may be connected to either a rotatable portion or a non-rotatable portion of the spindle 26. The spindle 26 may define a chamber 30 in fluid communication with the distal end D of the catheter C, which configuration allows for urine to drain out of the catheter C and into the chamber 30. The urine may subsequently be drained out of the catheter pack 10, as will be described in greater detail herein.

Figure 11:
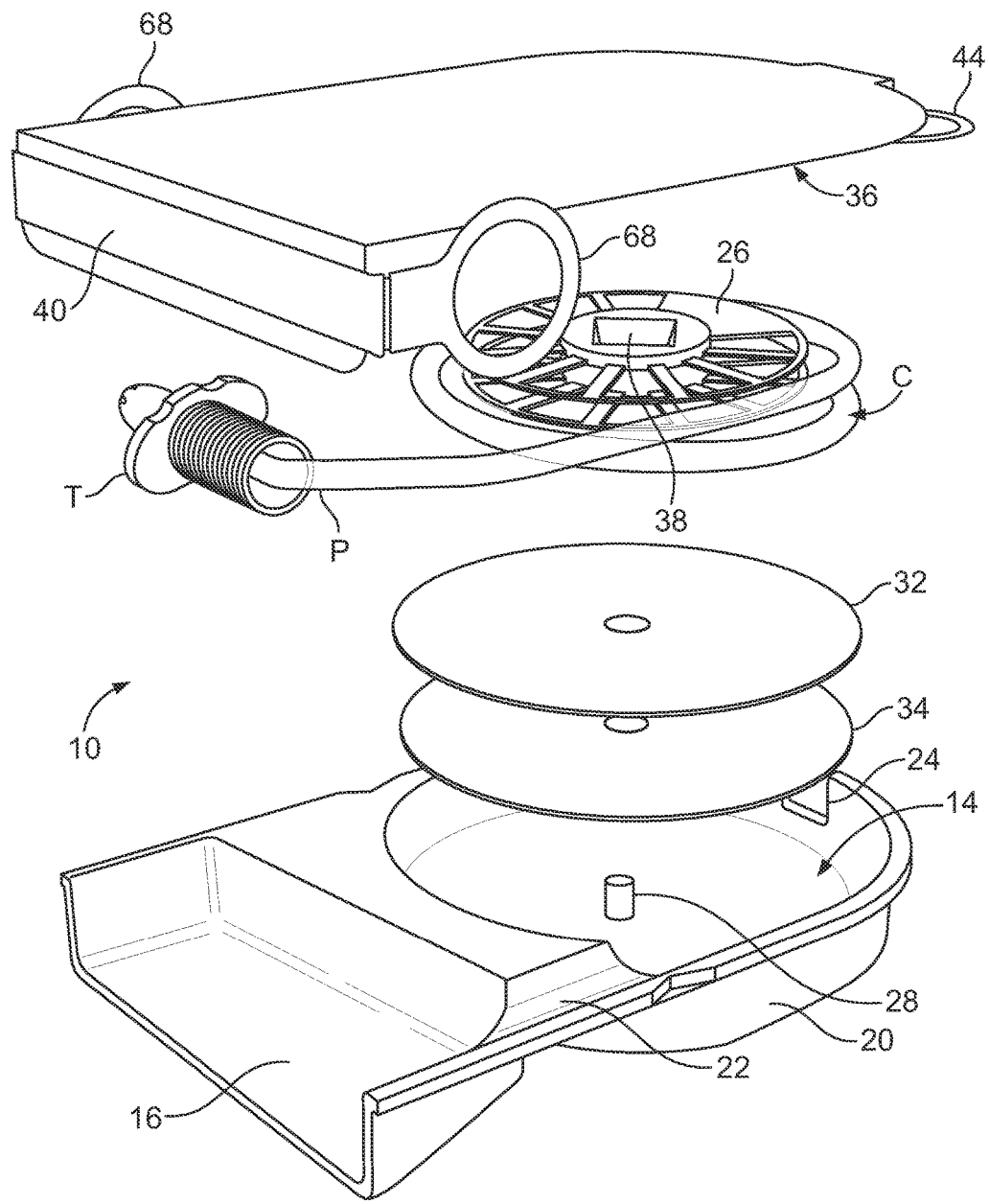
FIG. 11 is an exploded view of the various components of the catheter pack of FIG. 4.

In the illustrated embodiment, the spindle 26 and chamber 30 may be separated from the bottom wall 18 by a permeable layer 32 and/or a vapor insert or disk 34, as shown in FIG. 11. In one embodiment, the vapor disk 34 is treated with a vapor-donating fluid (e.g., water), while the permeable layer 32 acts as a barrier that prevents direct contact between the vapor disk 34 and the other components within the compartment 14. The permeable layer 32 may be secured to (e.g., by heat-sealing) the vapor disk 34 and/or the bottom wall 18 to isolate the vapor disk 34 from the other components within the compartment 14. The permeable layer 32 may be formed of calcium carbonate or a comparable material that allows vapor to pass from the vapor disk 34 into the compartment 14, where the vapor interacts with the catheter C. The catheter C may include a hydrophilic coating that, when exposed to vapor from the vapor disk 34, provides the catheter C with a lubricious surface, for increased comfort when the catheter C is advanced into a urethra. It may be advantageous to isolate the vapor disk 34 from the catheter C to prevent water droplets from forming on the catheter C or elsewhere within the compartment 14. In an alternative embodiment, the vapor disk 34 may be replaced with a vapor-permeable sachet, which may be disk-shaped for example, with the sachet being filled with a vapor-donating hydration fluid.

The catheter pack 10 further includes a cover 36 positioned opposite the bottom wall 18. The cover 36 is sealed against the upper ends of the sidewall 20 to effectively close the top of the compartments 14 and 16.

The spindle 26 may include a formed feature or cavity 38 (FIG. 7) facing the cover 36. In the illustrated embodiment, the feature 38 is a generally pyramid-shaped cavity (with the apex of the pyramid spaced from the cover 36 and the base of the pyramid positioned adjacent to the cover 36), but other configurations may be employed without departing from the scope of the present disclosure. The cover 36 is preferably manufactured from a material, such as a thin foil material, that may be deformed and/or pierced to access the cavity 38 through the cover 36 using an external device, as will be described in greater detail herein.

Figure 12:
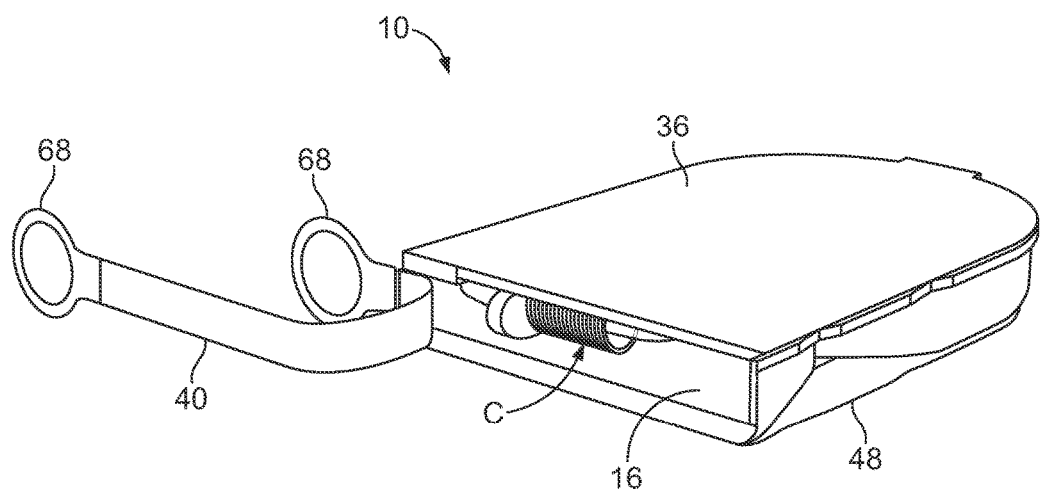
FIG. 12 is a perspective view of the catheter pack of FIG. 4, with a side cover partially removed to access a catheter within the catheter pack.

FIG. 5 illustrates an at least partially removable portion or side cover 40 of the catheter pack 10, with FIG. 12 showing the side cover 40 being partially removed. As shown in FIGS. 6-8, the sidewall 20 may extend only partially around the perimeter of the bottom wall 18, leaving a gap associated with the second interior compartment 16. The side cover 40 is sealed against the sidewall 20, bottom wall 18, and cover 36 (of which the side cover 40 may be an integrated or separate component) to effectively close the open portion or gap of the second interior compartment 16. As shown in FIG. 12, the side cover 40 may be at least partially detached to allow access into the second interior compartment 16 for removal of the catheter C therefrom, as will be described in greater detail herein. In other embodiments, the side cover 40 may be differently configured or omitted, depending on the configuration of the catheter pack 10.

Figure 13:
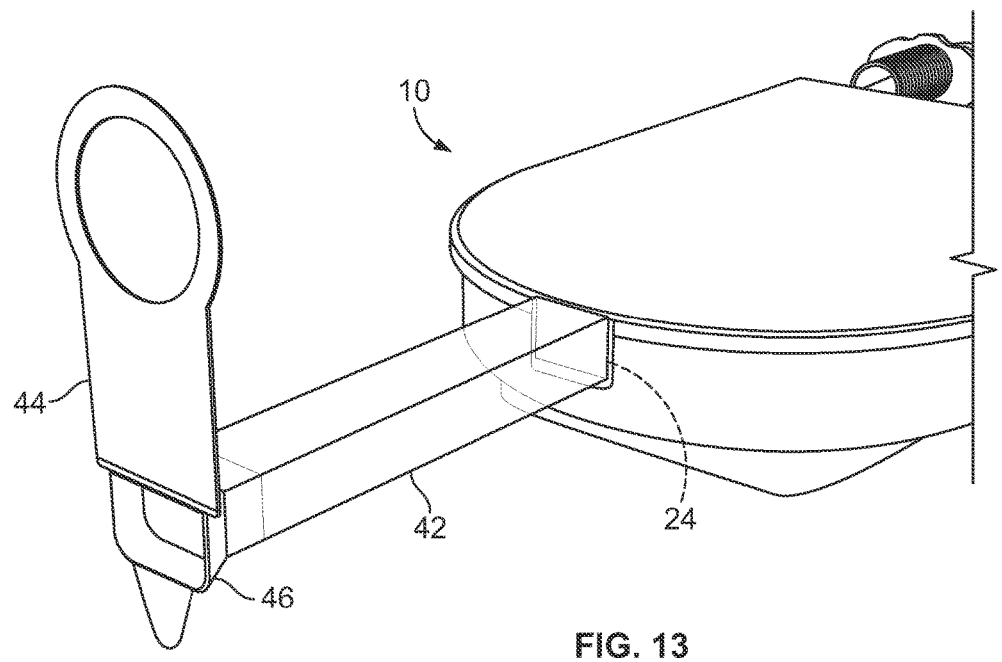
FIG. 13 is a perspective view of the catheter pack of FIG. 4, with a drainage channel extended from the catheter pack for draining urine from the catheter pack.
Figure 14:
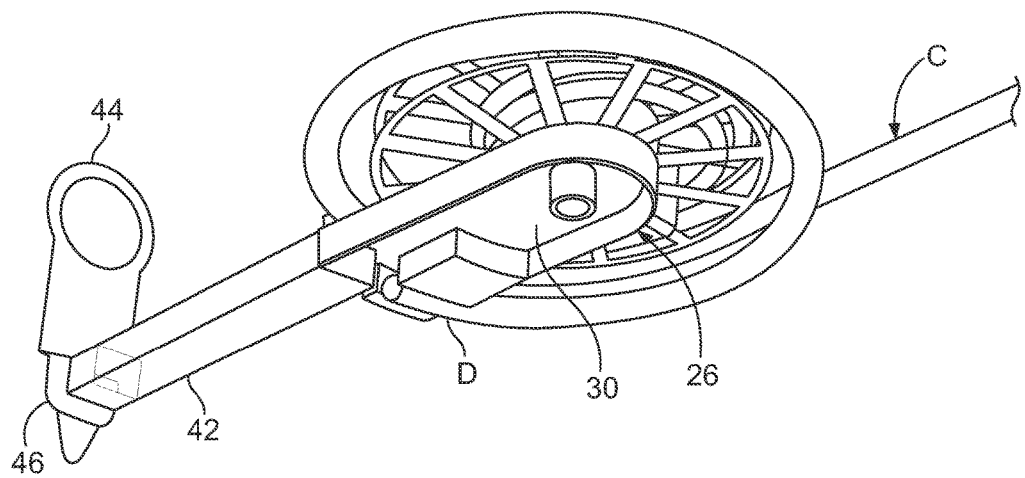
FIG. 14 is a bottom perspective view of the spindle, catheter, and drainage channel of the catheter pack of FIG. 4.

Returning now to the drainage opening 24 in the sidewall 20, it may receive an extendable drainage channel or tube 42 (FIGS. 13-14). The channel 42 may be substantially rigid or collapsible. If the channel 42 is rigid, it may move between a retracted position, in which it is at least partially (but, preferably, substantially entirely) received within the first interior compartment 14 (e.g., within the spindle chamber 30, if provided) and an extended position (FIG. 13), in which it is at least partially (but, preferably, substantially entirely) positioned outside of the first interior compartment 14. If provided, the channel 42 may include a removable or detachable cover flap 44 sealed to its outer end 46 to effectively close the channel 42 prior to use. FIG. 4 shows the cover flap 44 in a sealed condition, while FIG. 13 shows the cover flap 44 in an open or unsealed condition. FIGS. 13-14 show the channel 42 in an extended condition, but it should be understood that the channel 42 may be maintained within the catheter pack 10 prior to use. As will be explained in greater detail herein, the channel 42 may be used to drain urine from the first interior compartment 14 during and/or after use of the catheter pack 10. In other embodiments, which will be described in greater detail herein, other means may be provided for draining urine from a catheter pack, so it should be understood that the drainage opening 24 and channel 42 are optional features of a catheter pack according to the present disclosure.

Figure 15:
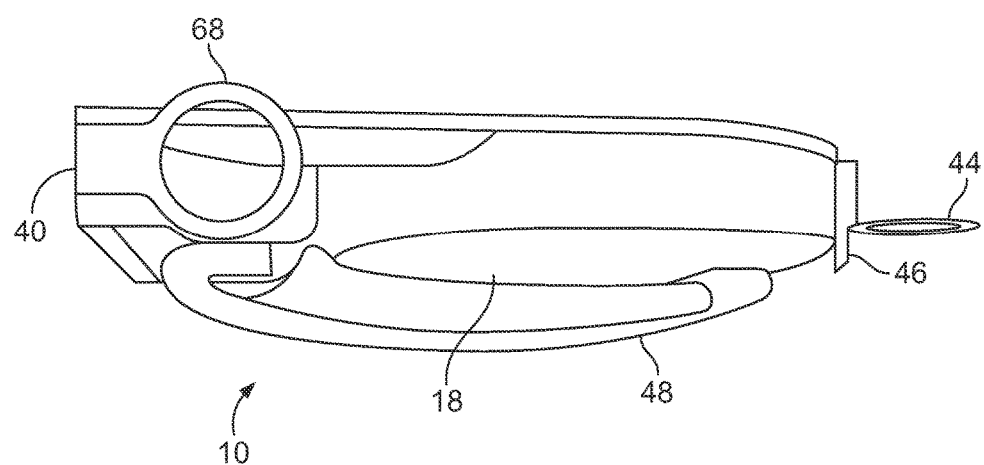
FIG. 15 is a side elevational view of the catheter pack of FIG. 4.

FIG. 15 shows the underside of the catheter pack 10, with a strap or retention feature 48 (illustrated as a hand strap) secured thereto. If provided, the hand strap 48 may be held by a user during use of the catheter pack 10 to stabilize and/or orient the catheter pack 10.

Figure 16:
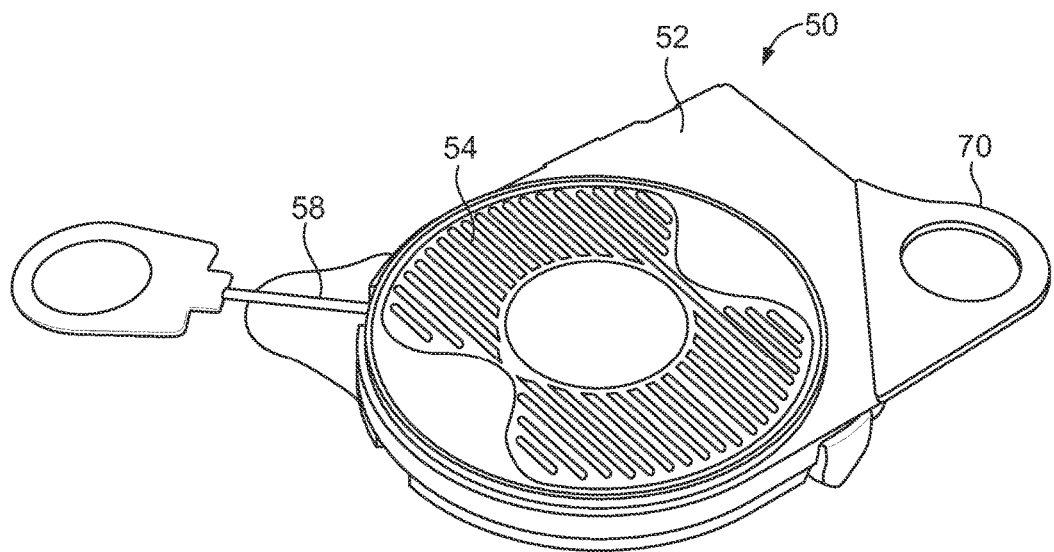
FIG. 16 is a perspective view of an introducer aid for use in combination with the catheter pack of FIGS. 4-15.
Figure 17:
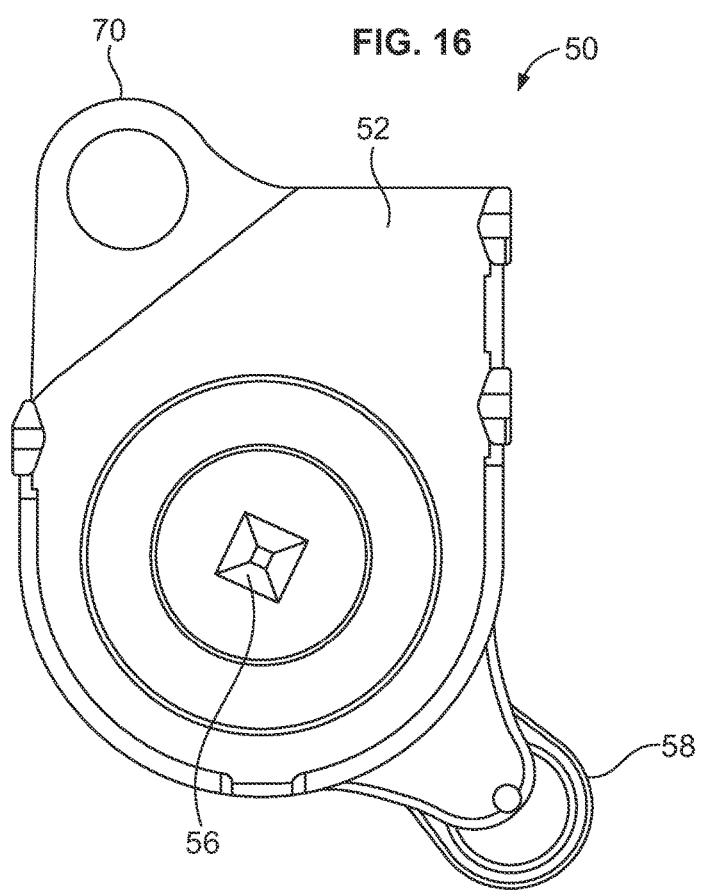
FIG. 17 is a bottom plan view of the introducer aid of FIG. 16.
Figure 18:
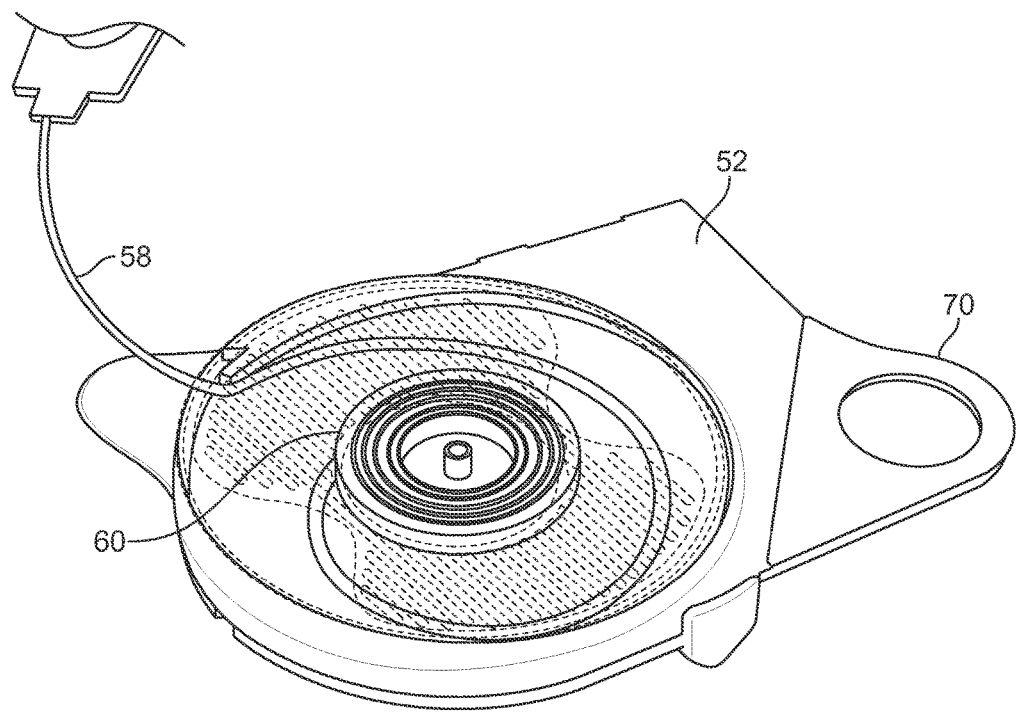
FIG. 18 is a perspective view of the introducer aid of FIG. 16, with a rotatable element thereof omitted for illustrative purposes.
Figure 22:
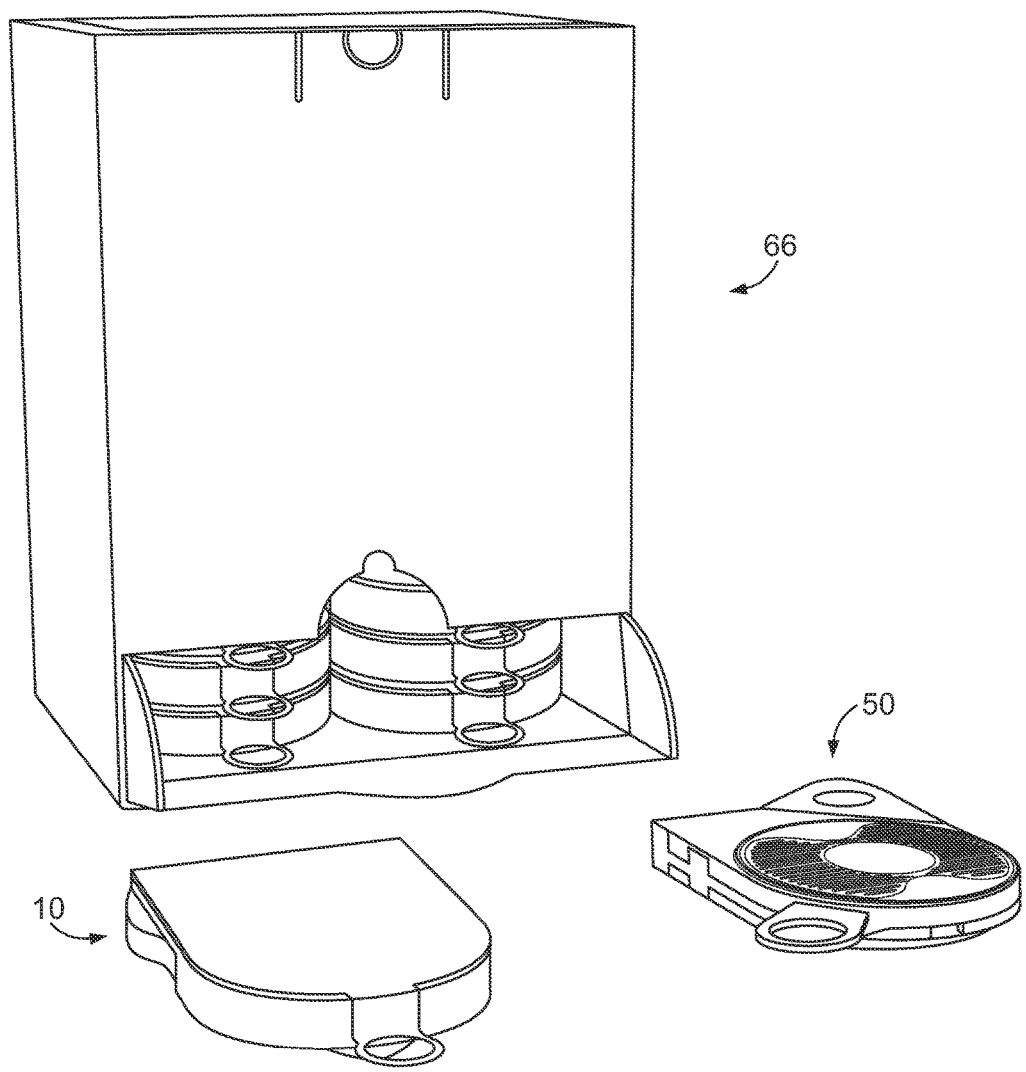
FIG. 22 is a perspective view of a container for storing a plurality of disposable catheter packs.

FIGS. 16-18 illustrate an exemplary embodiment of an introducer aid 50 that may be used in combination with the catheter pack 10 of FIGS. 4-15 to provide a urinary catheter deployment cassette or system 12 (FIGS. 19-22). The introducer aid 50 includes a base or body 52 with a rotatable element 54 on its upper side. The rotatable element 54 is illustrated as a disk, but it may be otherwise shaped without departing from the scope of the present disclosure. The rotatable element 54 may be provided with an audible feature, such that it makes a sound (e.g., a "clicking" noise) as it rotates.

The underside of the introducer aid 50 (FIG. 17) includes a spindle engagement member or projection 56. The spindle engagement member 56 is associated with the rotatable element 54 such that rotation of the rotatable element 54 rotates the spindle engagement member 56 to the same degree. The spindle engagement member 56 is shaped and configured to be received by the cavity 38 at the upper end of the spindle 26 of the catheter pack 10. Preferably, the spindle engagement member 56 is shaped and configured to engage the cavity 38 (either directly by piercing the cover 36 of the catheter pack 10 or indirectly by deforming the cover 36) and rotate the spindle 26 when the spindle engagement member 56 is pressed against the cover 36 and rotated. Most preferably, the spindle engagement member 56 has a shape that is complementary to the shape of the cavity 38 (e.g., a pyramid shape in the illustrated embodiment), but the spindle engagement member 56 may be otherwise configured without departing from the scope of the present disclosure.

As noted above, the spindle engagement member 56 may be rotated by rotating the rotatable element 54. The rotatable element 54 may be rotated by directly contacting it and rotating it around an axis (e.g., a central axis of the spindle engagement member 56) or by use of an associated pull string or draw string 58. At least a portion of the rotatable element 54 (e.g., the upper surface, as shown in FIG. 16) may be textured or otherwise configured for improved traction when rotating the rotatable element 54 by direct contact (e.g., by the hand of a user). FIG. 18 shows a portion of the rotatable element 54 omitted, with the pull string 58 wrapped around and secured to a central hub 60 of the rotatable element 54. By pulling the pull string 58 away from the introducer aid 50, the pull string 58 unwinds from the central hub 60, thereby causing the central hub 60, the rotatable element 54, and the spindle engagement member 56 to rotate about a common axis. Typically, using the pull string 58 causes the rotatable element 54 and the spindle engagement member 56 to rotate more quickly than when directly contacting and manually rotating the rotatable element 54. When the introducer aid 50 is provided with a pull string 58, the introducer aid 50 may include a mechanism for automatically retracting the pull string 58, such as a spring-operated retractor or retraction device, such that the pull string 58 is biased to its original position. Alternatively, the rotatable element 54 may be rotated (in a direction opposite to the direction in which it rotates in order to advance or pay out the catheter C) to retract the pull string 58.

FIGS. 19-21 show the introducer aid 50 being moved into cooperative engagement with the catheter pack 10. In particular, the introducer aid 50 is oriented with the underside of the introducer aid 50 (and, hence, the spindle engagement member 56) facing the cover 36 of the catheter pack 10. The underside of the introducer aid 50 is pressed against the cover 36 of the catheter pack 10, with the spindle engagement member 56 in alignment with the cavity 38 of the spindle 26. It may be preferable for the shapes of the introducer aid 50 and the catheter pack 10 to be provided so as to encourage or enforce proper alignment of the spindle engagement member 56 and the catheter pack 10, such that there is only one way in which the two may be fully pressed together. For example, as in the illustrated embodiment, one or both of the catheter pack 10 and the introducer aid 50 may include ribs or projections that can only be received in corresponding cavities or openings of the other device when the two devices are properly oriented with respect to each other.

FIG. 21 shows the catheter pack 10 and the introducer aid 50 fully connected to each other, with the spindle engagement member 56 at least partially received within the cavity 38 of the spindle 26. The spindle engagement member 56 deforms and/or pierces the cover 36 of the catheter pack 10 to move into the cavity 38 of the spindle 26. One or both of the catheter pack 10 and the introducer aid 50 may include features that allow the catheter pack 10 and the introducer aid 50 to be temporarily retained or locked together when the spindle engagement member 56 has been at least partially received within the cavity 38 of the spindle 26, such as the extending clip or rim 62 of the catheter pack 10 and the groove or lip 64 of the introducer aid 50 (FIG. 20) that receives the clip or rim 62. With the catheter pack 10 and the introducer aid 50 so joined as shown in FIG. 21, the spindle 26 may be rotated by rotating the rotatable element 54 of the introducer aid 50.

FIGS. 23-26 show an exemplary method of using the urinary catheter deployment cassette or system 12. First, a user obtains a catheter pack 10 and an introducer aid 50. In one embodiment, the catheter pack 10 is a single-use item, while the introducer aid 50 is a more durable item, which is intended for repeated use. In other examples, both of the items may be intended for single use or for multiple use, or the catheter pack 10 may be intended for reloading and reuse, while the introducer aid 50 is a single-use item. In the event that the catheter pack 10 is a single-use item, as in a preferred embodiment, a plurality of catheter packs 10 may be provided in a container or housing 66 (FIG. 22), with the user obtaining a single catheter pack 10 from the container 66 prior to use.

Figure 23:
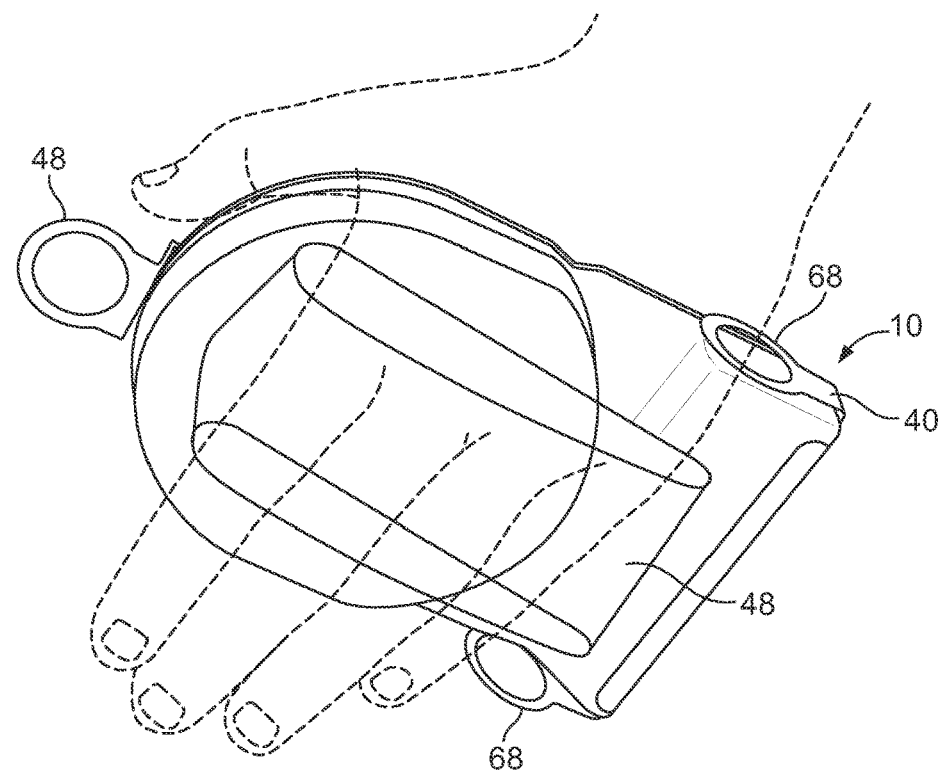
FIG. 23 is a bottom perspective view of the catheter pack of FIGS. 4-15, with the hand of a user holding a strap of the catheter pack.
Figure 24:
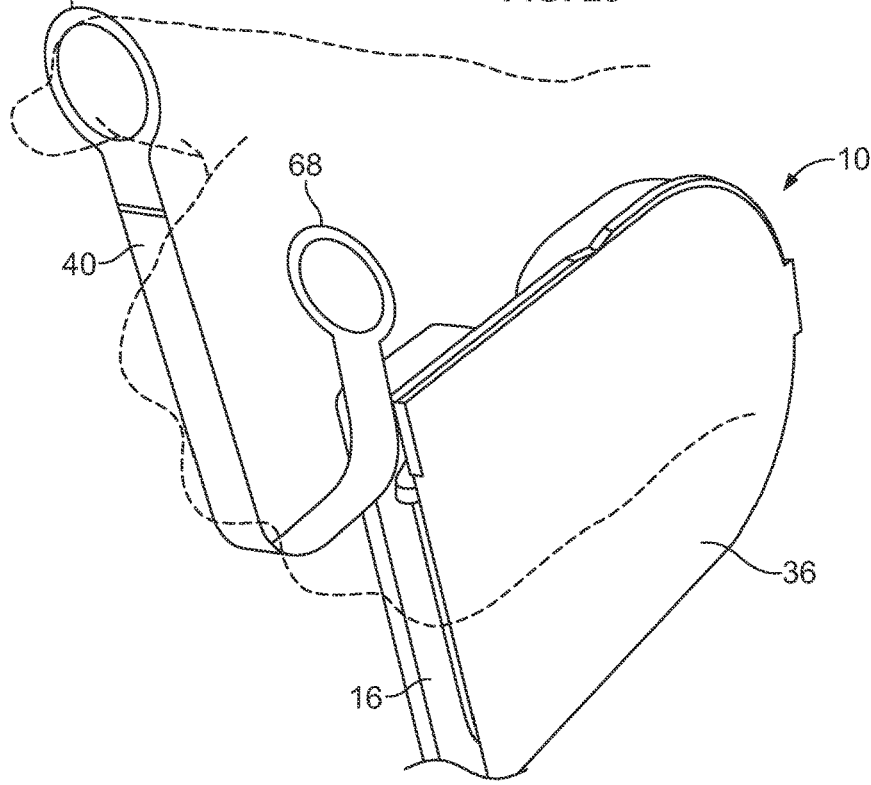
FIG. 24 is a perspective view of a user removing the side cover from the catheter pack of FIGS. 4-15.
Figure 25:
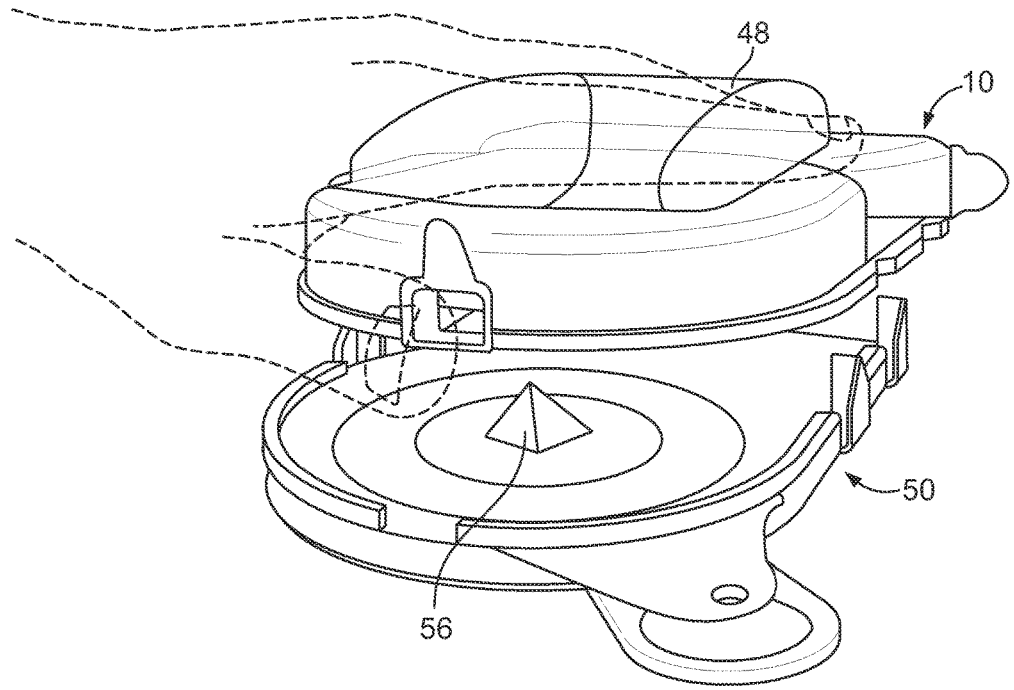
FIG. 25 is a perspective view of a user moving the catheter pack of FIGS. 4-15 into engagement with the introducer aid of FIGS. 16-18.

The user grips or otherwise engages the catheter pack 10 (e.g., using the hand strap 48, if provided, as shown in FIG. 23) and at least partially removes the side cover 40 (FIG. 24) to allow access to the interior of the catheter pack 10 via the second interior compartment 16. As shown in FIG. 24, the side cover 40 may include one or more formations (e.g., a tab or annular thumb loop 68) to allow a user to more easily remove or detach the side cover 40. In the illustrated embodiment, the side cover 40 includes thumb loops 68 at opposite ends of the side cover 40, thereby allowing for either right- or left-hand manipulation and removal of the side cover 40.

With the side cover 40 at least partially detached, the user presses the spindle engagement member 56 of the separate introducer aid 50 into the cavity 38 of the spindle 26 of the catheter pack 10 (FIG. 25) until the catheter pack 10 and the introducer aid 50 are temporarily secured together to define the urinary catheter deployment cassette or system 12, as described above in greater detail. One or both of the devices may be provided with graphical indicia to help orient the introducer aid 50 with respect to the catheter pack 10. Additionally, only a portion of the cover 36 of the catheter pack 10 may be deformable or pierceable or may be more deformable or pierceable than other portions of the cover 36 (e.g., the portion overlaying the spindle 26 may be the only deformable or pierceable portion of the cover 36), to prevent deformation or piercing of an improper location of the cover 36.

With the catheter pack 10 and the introducer aid 50 connected to form the urinary catheter deployment cassette or system 12 (FIG. 26), the rotatable element 54 of the introducer aid 50 may be rotated to rotate the spindle engagement member 56 which, in turn, rotates the spindle 26, as described above in greater detail. By so rotating the spindle 26, the catheter C is advanced or paid out from the interior of the catheter pack 10 via the open portion of the second interior compartment 16 that is exposed by detaching the side cover 40 (if provided). In one embodiment, the catheter C is configured and positioned within the catheter pack 10 such that the protective tip T and at least a portion of the proximal end P will automatically move outside of the catheter pack 10 upon detachment of the side cover 40, without having to rotate the spindle 26.

With at least the protective tip T and a portion of the proximal end P of the catheter C positioned outside of the catheter pack 10, the proximal end P of the catheter C may be advanced into the urethra by proper alignment of the catheter C and use of the rotatable element 54. It may be advantageous for the user to directly contact and rotate the rotatable element 54 initially to more slowly advance or pay out the catheter C from the catheter pack 10 and ensure proper introduction of the catheter C into the urethra. When the user is assured that the catheter C has been properly introduced into the urethra, the pull string 58 may be used to more quickly rotate the rotatable element 54 and advance or pay out the catheter C to its final insertion location, with the proximal end P of the catheter C positioned within the bladder.

Figure 26:
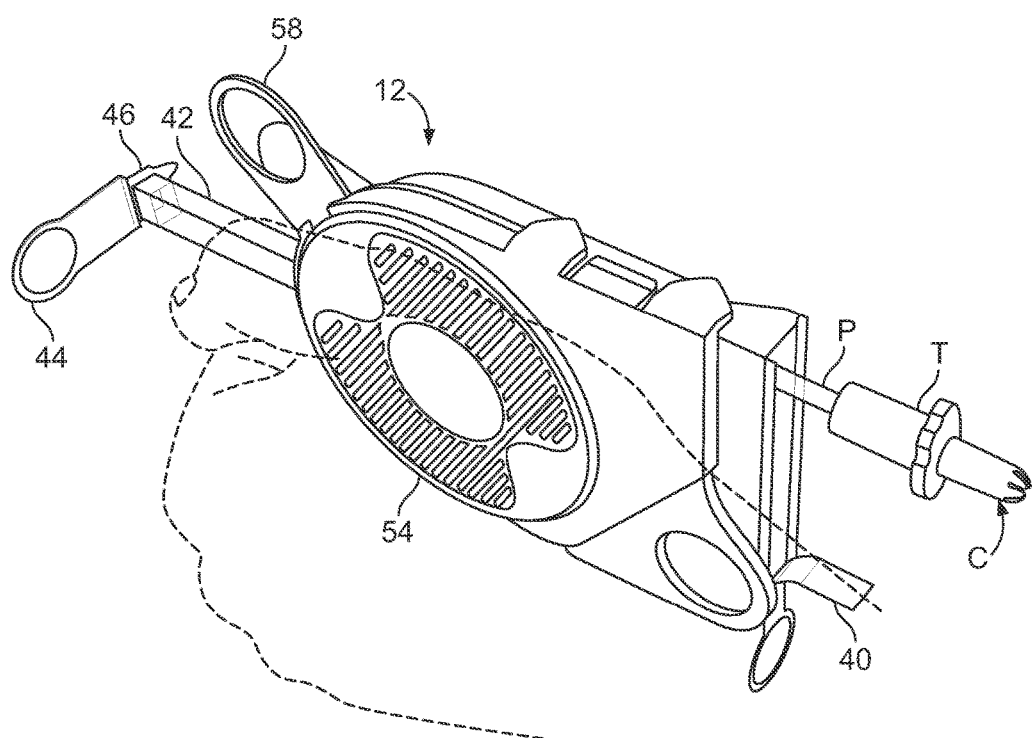
FIG. 26 is a perspective view of a user advancing a catheter out of the catheter pack of FIGS. 4-15 using the introducer aid of FIGS. 16-18.

With the catheter C properly positioned, the cover flap 44 of the catheter pack 10 may be opened or unsealed, and then the channel 42 may be extended, as shown in FIG. 26. Urine flowing through the catheter C enters the interior of the catheter pack 10, to a location in fluid communication with the channel 42 (e.g., the spindle chamber 30). The channel 42 drains the urine from the interior of the catheter pack 10 into a toilet or other disposal location.

When the user is done with the urinary catheter deployment cassette or system 12, the catheter C is retracted from the urethra into the catheter pack 10 by rotating the rotatable element 54 in the opposite direction of the direction in which it was initially rotated to advance or pay out the catheter C. Alternatively, the catheter C may be removed from the urethra by moving the urinary catheter deployment cassette or system 12 in a distal direction away from the urethra. With the catheter C fully removed from the urethra, the introducer aid 50 may be detached from the catheter pack 10 by moving the two devices away from each other in a direction opposite to the direction in which they were initially moved to join them. Detachment of the introducer aid 50 from the catheter pack 10 may be simplified by providing one or both devices with a removal aid, such as the thumb ring or loop 70 of the illustrated introducer aid 50 (FIG. 16), that may be gripped by a user following use of the urinary catheter deployment cassette or system 12. Finally, the catheter pack 10 may be disposed of, while the introducer aid 50 is retained for subsequent use with another catheter pack 10 (if the catheter pack 10 is disposable and the introducer aid 50 is reusable, as in a preferred embodiment). If the introducer aid 50 is to be reused, it is preferred for urine flowing through the catheter pack 10 to avoid contact with the spindle engagement member 56, such that the introducer aid 50 is not contaminated by urine during use.

Urinary catheter deployment cassettes or systems according to the foregoing description have a number of advantages. For example, the user is not required to grip or directly handle the catheter during use, thereby reducing the risk of contamination. Also, the cassette or system can be easily used by a person with limited dexterity, while also providing a consistent routine for catheterization. Furthermore, the catheter itself is provided in a package (which may be hydrophilic) that is compact and discrete, such that a user could conceal the catheter pack (and the catheter housed therein) prior to use.

Figure 27:
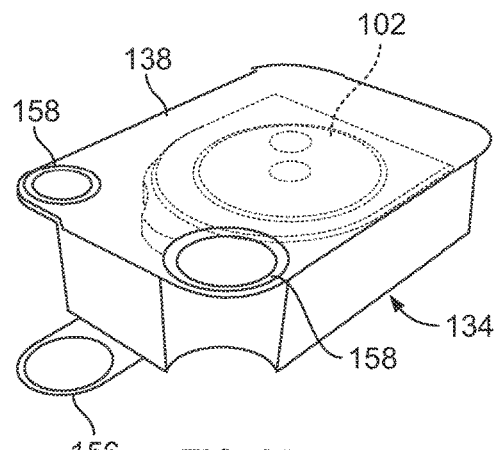
FIG. 27 is a perspective view of an alternative embodiment of a packaged catheter pack of a urinary catheter deployment system or cassette according to another aspect of the present disclosure.
Figure 28:
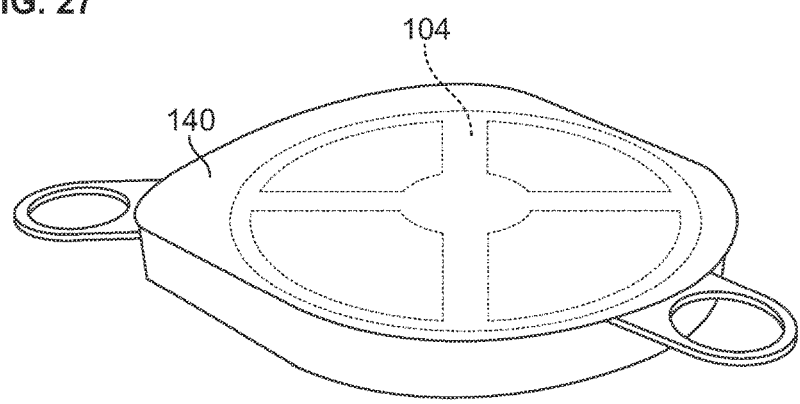
FIG. 28 is a perspective view of a packaged drainage adaptor for use in combination with the catheter pack of FIG. 27.

FIGS. 27-53 illustrate another embodiment of a urinary catheter deployment cassette or system 100 (FIG. 37) having these same benefits. FIGS. 27 and 28 show a packaged catheter pack 102 (FIG. 27) and a packaged drainage adaptor 104 (FIG. 28) of the urinary catheter deployment cassette or system 100. The catheter pack 102 is shown in greater detail in FIGS. 29-34, while the drainage adaptor 104 is shown in greater detail in FIGS. 35 and 36. The combined catheter pack 102 and drainage adaptor 104 (i.e., the urinary catheter deployment cassette or system 100) are shown in FIGS. 37-41. FIGS. 42-53 illustrate an exemplary embodiment of a method of using the urinary catheter deployment cassette or system 100.

The catheter pack 102 includes a base or body 106 with a rotatable element 108 associated therewith. The rotatable element 108 is illustrated as a disk associated with the upper surface of the catheter pack body 106, but it may be otherwise shaped and positioned without departing from the scope of the present disclosure. The rotatable element 108 may be provided with an audible feature, such that it makes a sound (e.g., a "clicking" noise) as it rotates.

The rotatable element 108 includes a downwardly extending projection or spindle 110 (FIG. 33) that enters into the interior compartment 112 of the catheter pack 102 via an opening or aperture in the upper surface of the catheter pack body 106. The spindle 110 is associated with the rotatable element 108 such that rotation of the rotatable element 108 rotates the spindle 110 to the same degree. A pusher 114 is associated with the spindle 110 for rotation with the spindle 110. In the illustrated embodiment, the pusher 114 includes an arm 116 that extends radially outwardly from the spindle 110 and a catheter-engagement portion 118 associated with the pusher arm 116 at a position spaced radially outwardly of the spindle 110. The pusher arm 116 may have an intermediate rigidity, allowing it to be sufficiently rigid to engage and press a catheter C along a generally helical guide or track 120 positioned within the compartment 112, while also being sufficiently flexible to follow along the track 120 as the elevation of the track 120 with respect to the pusher arm 116 changes. The way in which the pusher 114 and track 120 cooperate to deploy a catheter C will be described in greater detail herein.

Figure 33:
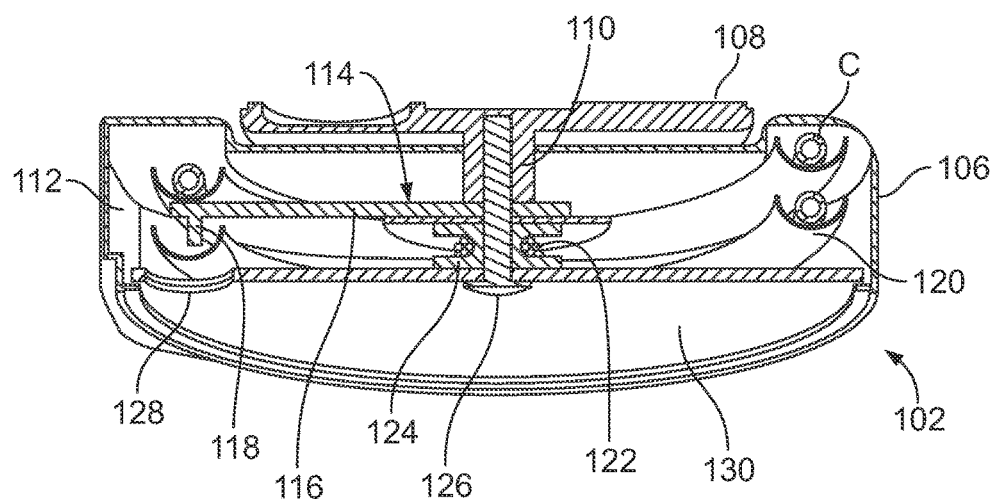
FIG. 33 is a cross-sectional view of the catheter pack of FIG. 30.
Figure 34:
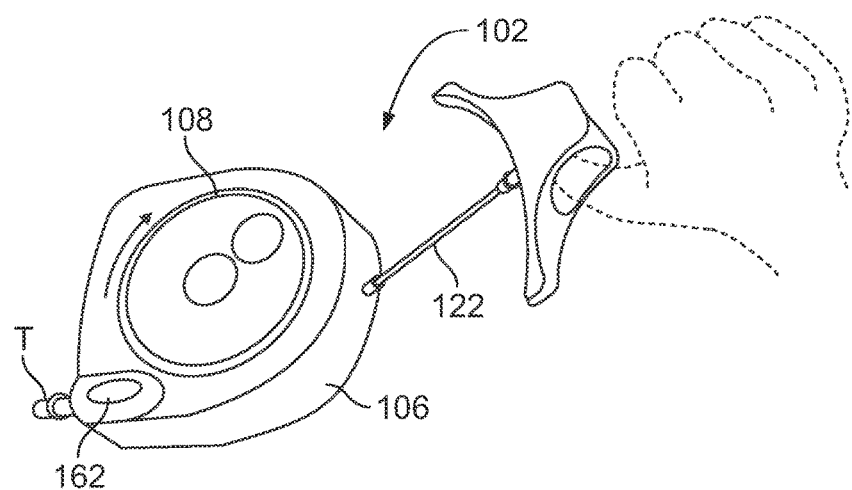
FIG. 34 is a perspective view of the catheter pack of FIG. 30, with a pull string of the catheter pack partially advanced out of the catheter pack.

The spindle 110 and pusher 114 may be rotated by rotating the rotatable element 108, either by directly contacting it and spinning it around an axis (e.g., a central axis of the spindle 110) or by use of an associated pull string or draw string 122 (FIG. 34). At least a portion of the rotatable element 108 (e.g., its upper surface) may be textured or otherwise configured for improved traction by the hand of a user for rotation by directly contacting the rotatable element 108. FIG. 33 shows a cross-section of the catheter pack 102, with the pull string 122 wrapped around and secured to a central hub 124 associated with the pusher 114, although it is also within the scope of the present disclosure for the pull string 122 to be wrapped around and secured to the spindle 110. If provided, the central hub 124 may be secured to the pusher 114, such that rotation of the rotatable element 108 serves to rotate the central hub 124 and vice versa. A shaft or stem 126 may pass through openings or apertures of the pusher 114 and central hub 124 and be received within a cavity of the spindle 110 to help align the spindle 110, the pusher 114, and the central hub 124 and to simplify assembly of the catheter pack 102.

By pulling the pull string 122 away from the catheter pack 102, the pull string 122 unwinds from the central hub 124 and/or the spindle 110, thereby causing the rotatable element 108 and the pusher 114 to rotate about a common axis. Typically, using the pull string 122 causes the rotatable element 108 and the pusher 114 to rotate more quickly than when directly contacting and rotating the rotatable element 108 by hand.

The track 120 of the illustrated catheter pack 102 extends between a first or lower opening 128 defined in the bottom wall or surface 130 of the catheter pack 102 (FIG. 32) and a second or upper opening 132 (FIG. 30) defined in a sidewall of the catheter pack 102. The track 120 defines a generally helical path through the interior compartment 112 of the catheter pack 102 that is traversed by at least a portion of the catheter C during use of the urinary catheter deployment cassette or system 100. In contrast to the first embodiment, the catheter C and the means for deploying the catheter C are both incorporated into the catheter pack 102, rather than having a separate introducer aid. In particular, the catheter-engagement portion 118 of the pusher 114 contacts a distal portion or end D of the catheter C and pushes the catheter C along the track 120 as the pusher 114 is rotated (by either rotating the rotatable element 108 or pulling the pull string 122). Sufficient advancement of the catheter C along the track 120 causes the proximal end P of the catheter C to exit the catheter pack 102 via the second opening 132 for introduction into the urethra. The pusher 114 may provide a positive stop or impediment that allows only a portion of the catheter C to be deployed from the catheter pack 102, while preventing complete removal of the catheter C from the catheter pack 102. While it may be advantageous for the catheter pack 102 to include a generally helical track 120 to guide the catheter C out of the catheter pack 102 during use, it is also within the scope of the present disclosure for the track 120 to have a different shape or for a track 120 to be omitted from the catheter pack 102.

The second opening 132 of the catheter pack 102 may be configured to receive a separately provided protective tip T that may be loaded into and temporarily retained within the second opening 132 after the catheter pack 102 has been removed from its container 134. The protective tip T may be provided in a cap 136 that may be handled without directly contacting the protective tip T. Prior to use, the cap 136 (with the protective tip T loaded therein) is pressed into the second opening 132, such that at least a portion of its body portion B is retained within the second opening 132, while at least the access end A is positioned outside of the catheter pack 102. Subsequently, the cap 136 is removed (FIG. 34) to expose the protective tip T, which is eventually engaged by the proximal end P of the catheter C as the catheter C is advanced along the track 120 to the second opening 132, as described above.

The lower opening 128 allows for urine to drain from the catheter C and/or the interior compartment 112 into the associated drainage adaptor 104, as will be described in greater detail herein. If the track 120 is configured to extend between the lower and upper openings 128 and 132 of the catheter pack 102, then the track 120 may guide or direct urine from the catheter C to the lower opening 128. The bottom wall 130 of the catheter pack 102 may be configured to assist in directing urine drained through the catheter C to the lower opening 128, such as by having slanted surfaces that define a funnel centered about the lower opening 128. Additionally, the bottom wall 130 may include a permeable layer and vapor disk or sachet (not illustrated), similar to the permeable layer 32 and the vapor disk 34 of the first embodiment, for hydrating and lubricating the catheter C positioned within the catheter pack 102.

Figure 29:
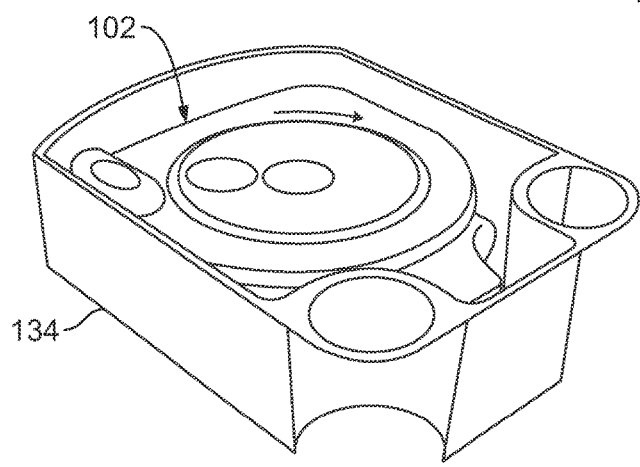
FIG. 29 is a perspective view of the packaged catheter pack of FIG. 27, with a cover or lid of the container removed for accessing the catheter pack.
Figure 30:
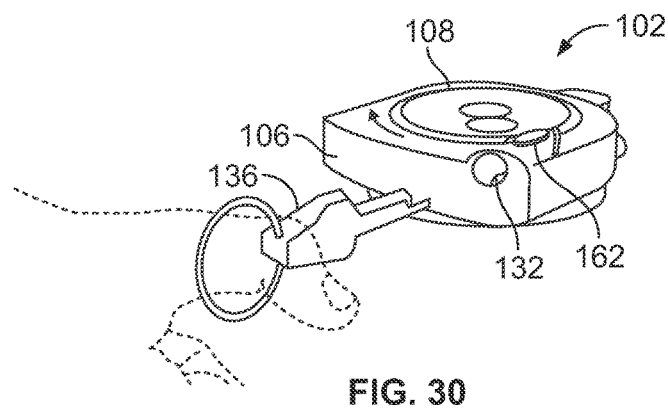
FIG. 30 is a perspective view of the catheter pack of FIG. 27, removed from its container.
Figure 31:
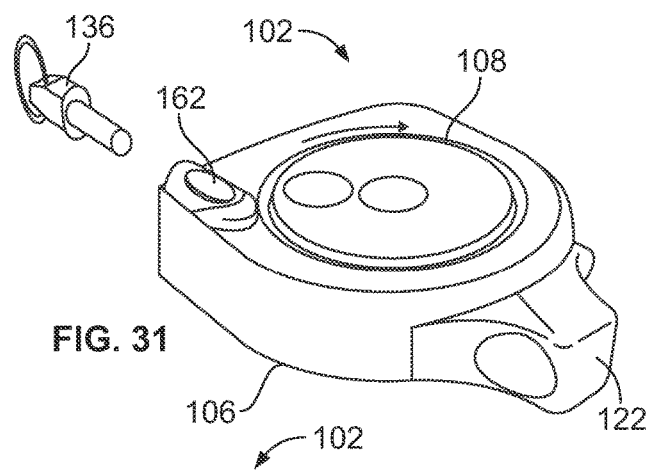
FIG. 31 is a rear perspective view of the catheter pack of FIG. 30.
Figure 32:
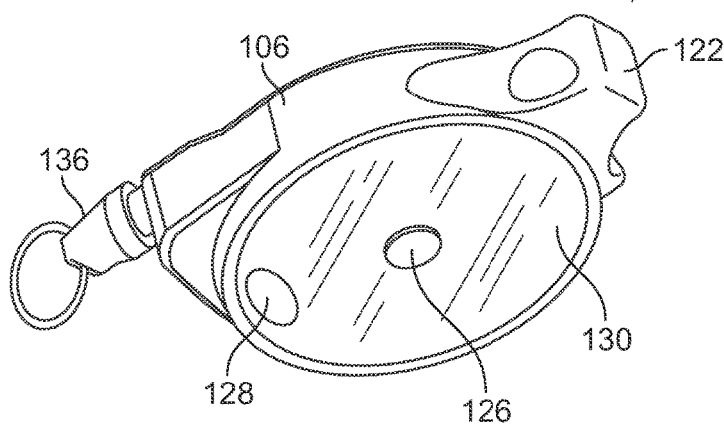
FIG. 32 is a bottom perspective view of the catheter pack of FIG. 30.

It may be advantageous to maintain the catheter pack 102 in a sterile environment prior to use. FIGS. 27 and 29 illustrate an exemplary container or housing 134 for the catheter pack 102. The catheter pack 102 may be maintained within the container 134 prior to use, with a cover or lid 138 of the container 134 being at least partially detachable to remove the catheter pack 102 for use with the drainage adaptor 104 (as will be described in greater detail below). If the catheter pack 102 is intended to be reused, then the cover or lid 138 may be resealably associated with the container 134; otherwise, if the catheter pack 102 is intended as a single-use item, then the cover or lid 138 may be permanently detachable from the container 134 to access the catheter pack 102.

Figure 35:
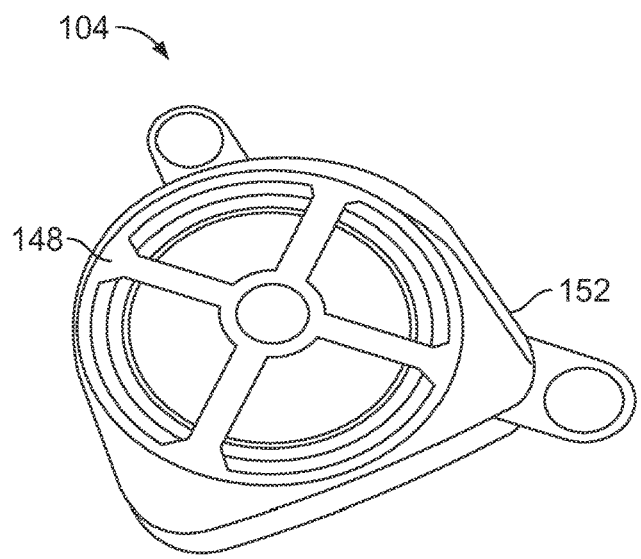
FIG. 35 is a perspective view of the drainage adaptor of FIG. 28, with a cover or lid removed to allow use of the drainage adaptor with the catheter pack of FIGS. 30-34.
Figure 36:
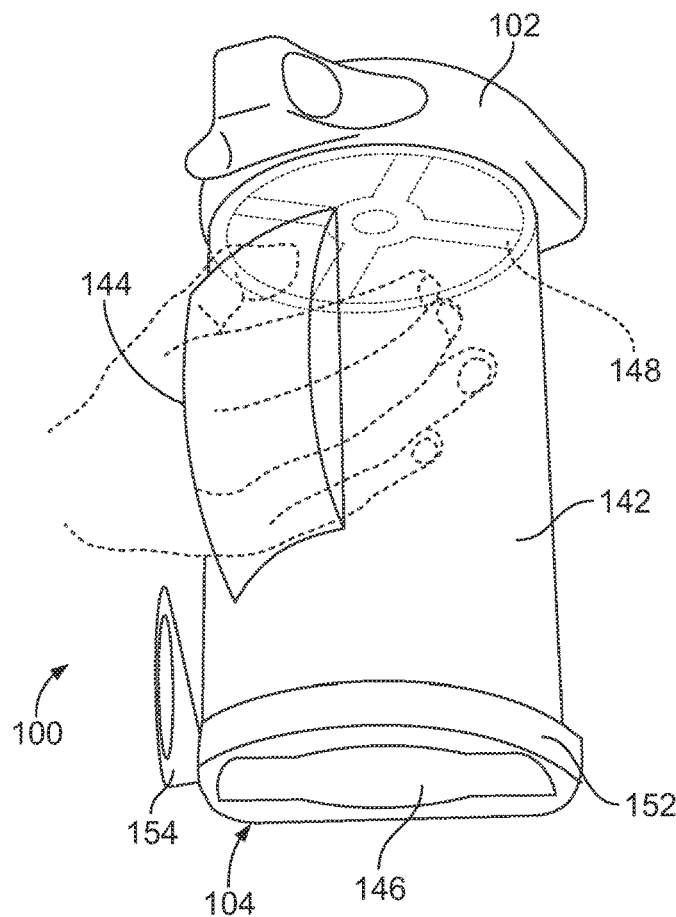
FIG. 36 is a perspective view of the drainage adaptor of FIG. 35, with a collection bag of the drainage adaptor is a deployed or expanded condition.
Figure 37:
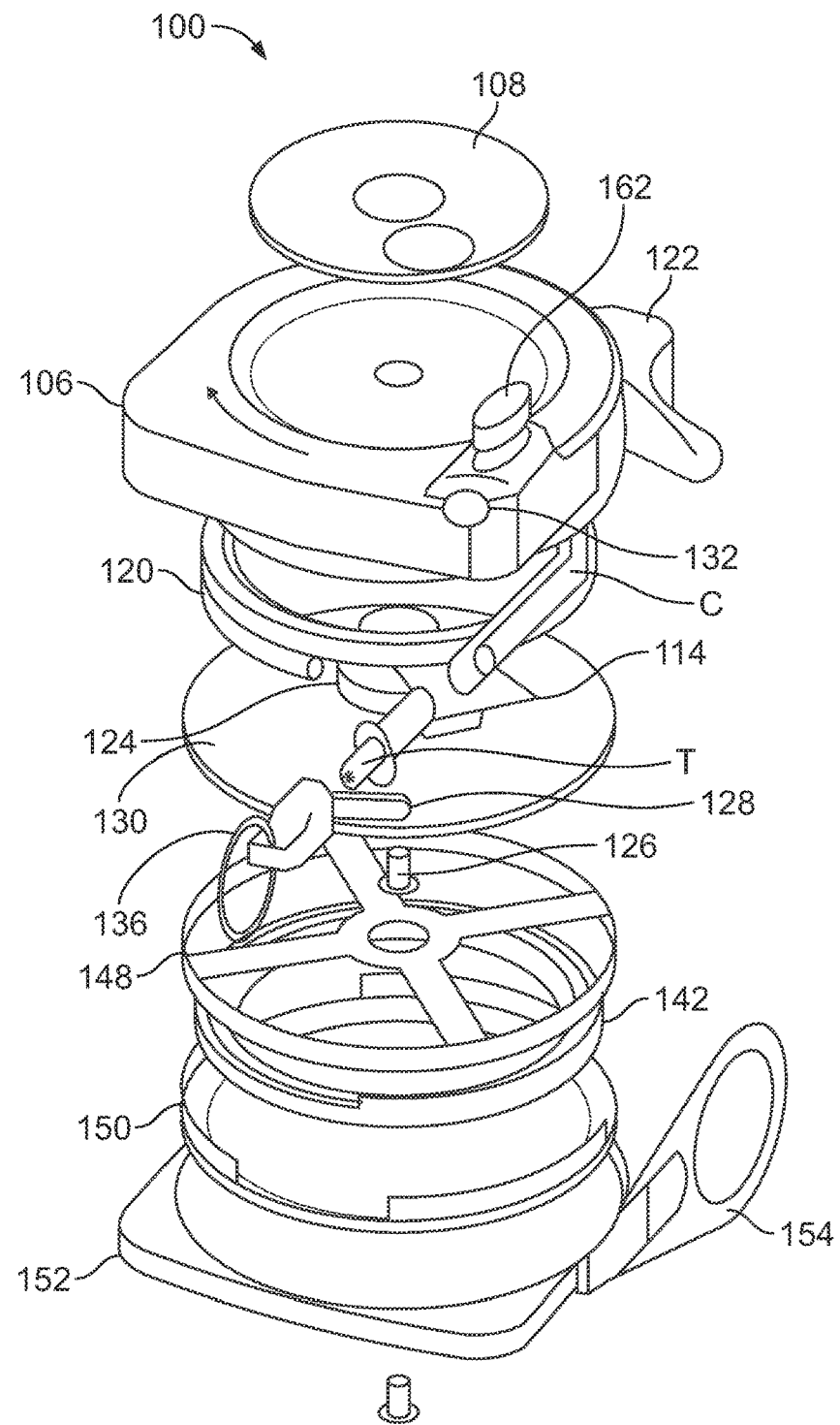
FIG. 37 is an exploded view of the catheter pack of FIGS. 30-34 and the drainage adaptor of FIGS. 35 and 36.
Figure 38:
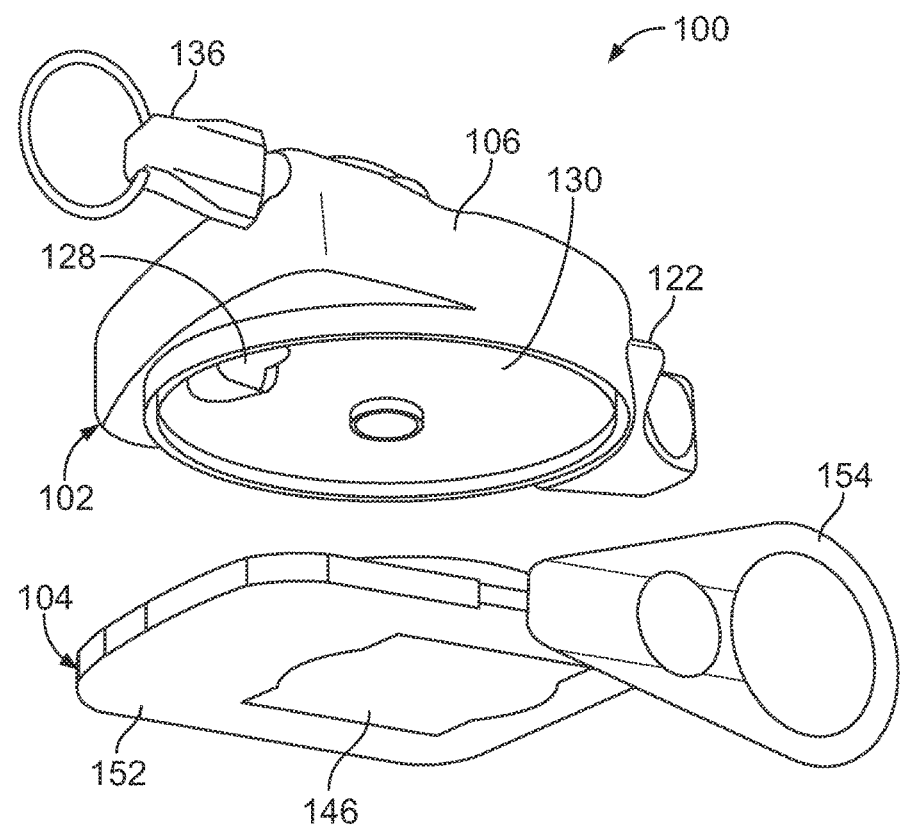
FIG. 38 is a bottom perspective view of the catheter pack of FIGS. 30-34 being moved into engagement with the drainage adaptor of FIGS. 35 and 36.
Figure 39:
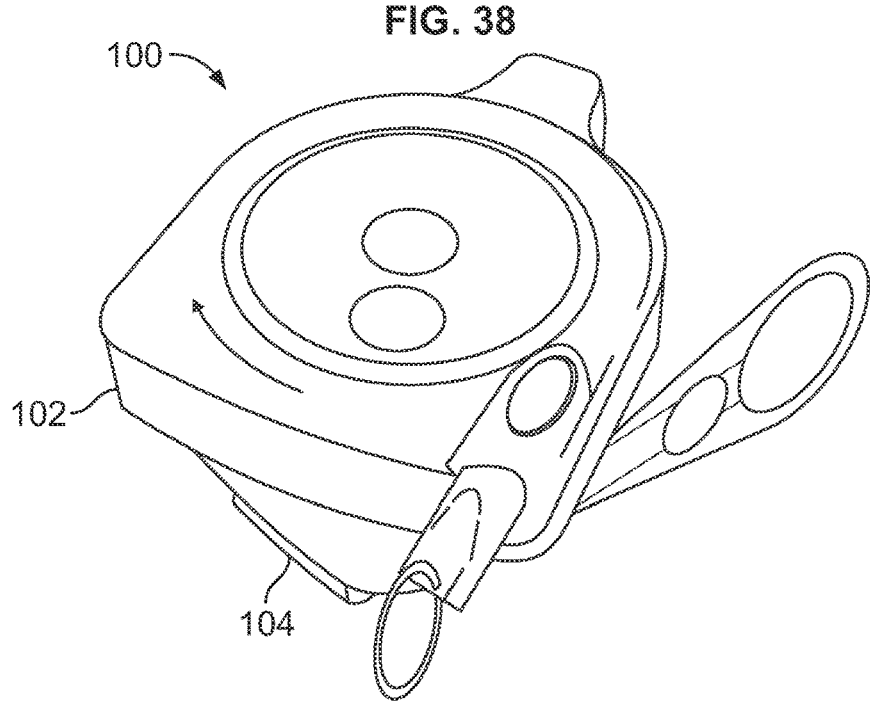
FIG. 39 is a perspective view of the catheter pack of FIGS. 30-34 in engagement with the drainage adaptor of FIGS. 35 and 36, with the catheter pack out of alignment with the drainage adaptor.
Figure 40:
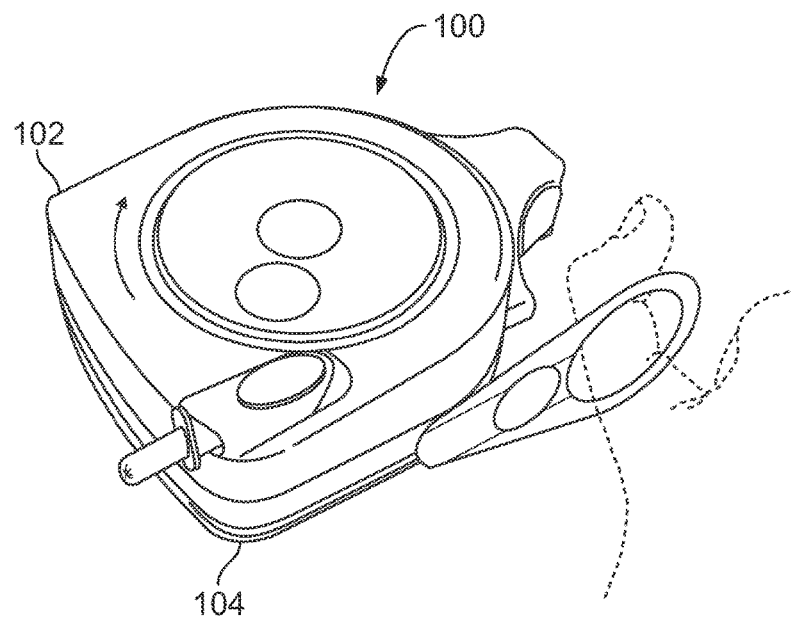
FIG. 40 is a perspective view of the catheter pack and drainage adaptor of FIG. 39, with the catheter pack and drainage adaptor aligned to define a deployment cassette or system.
Figure 41:
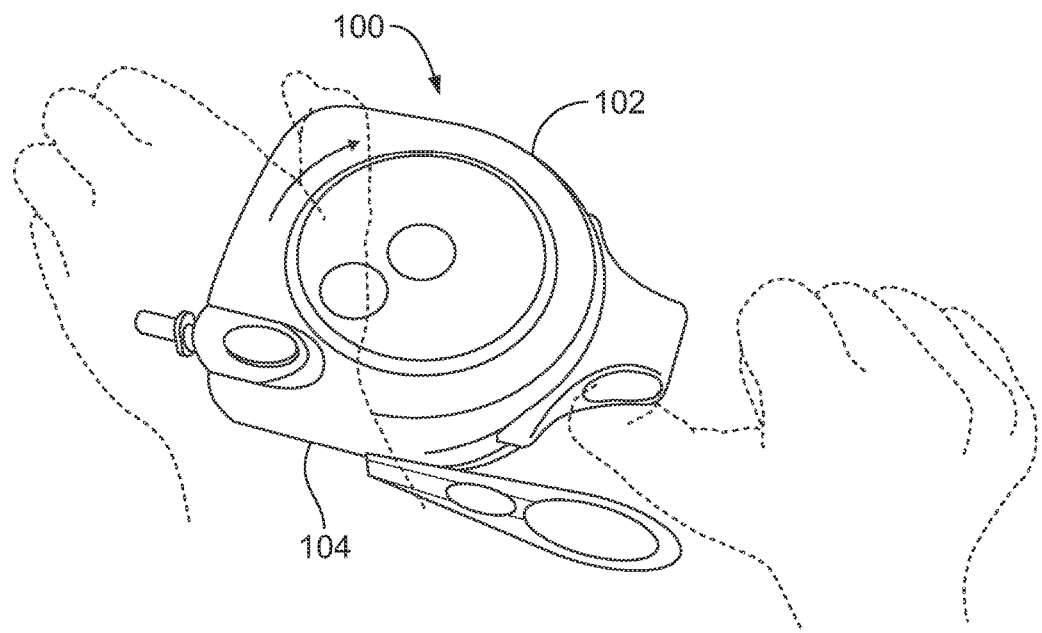
FIG. 41 is a perspective view of the deployment system of FIG. 40, with a user deploying a catheter from the catheter pack of the system.

FIGS. 35 and 36 illustrate the drainage adaptor 104 with a cover or lid 140 (FIG. 28) removed therefrom. The drainage adaptor 104 includes a collapsible collection bag 142 (FIG. 36) that may be moved from a collapsed condition (FIG. 35) to an expanded condition (FIG. 36). In the collapsed condition, the collection bag 142 is stored in the drainage adaptor 104 prior to use without significantly increasing the height or size of the drainage adaptor 104. The collection bag 142 may include labels, markings, or graphics to show the amount of urine contained therein, and may also include a built-in handle or strap 144 to aid in holding the collection bag 142 during use of the urinary catheter deployment cassette or system 100. The bottom of the drainage adaptor 104 may include an engagement feature 146 (FIG. 36) configured to retain the bottom of the drainage adaptor 104 in place against a toilet or other surface. In one embodiment, the engagement feature 146 may be comprised of a sticky or adhesive material that temporarily holds the bottom of the drainage adaptor 104 in position against a surface, but also allows for the bottom of the drainage adaptor 104 to be removed from the associated surface as desired.

In the illustrated embodiment, the collection bag 142 extends between an upper end or frame 148 and a lower end or frame 150 (FIG. 37), with the lower frame 150 being secured to the body or base 152 of the drainage adaptor 104 and the upper frame 148 being movable away from the drainage adaptor body 152. In one embodiment, the upper frame 148 may be freely movable away from the drainage adaptor body 152 to expand the collection bag 142 whereas, in other embodiments, the drainage adaptor 104 may incorporate a release feature (e.g., a pull tab or the like) that may be manipulated to release the upper frame 148 from the body 152 to expand the collection bag 142.

The frames 148 and 150 may be differently sized to allow the smaller one to fit or nest within the larger one when the collection bag 142 is in a collapsed condition (as in FIG. 35, where the upper frame 148 is larger than the lower frame 150) to reduce the total height of the drainage adaptor 104 prior to use. The upper frame 148 is configured to be received by the underside of the catheter pack 102 during use, as shown in FIG. 36. The upper frame 148 includes at least one opening to allow fluid from the catheter C of the catheter pack 102 to drain out of the catheter pack 102 via the lower opening 128 and into the collection bag 142, as will be described in greater detail herein.

The drainage adaptor body 152 may further include a pull tab 154 (FIG. 36) or other drain actuator that may be pulled or otherwise actuated by a user to drain urine out of the collection bag 142, as will be described in greater detail herein.

Similar to the catheter pack 102, it may be advantageous to maintain the drainage adaptor 104 in a sterile environment prior to use. For example, FIG. 28 shows the drainage adaptor 104 with a removable lid or cover 140 secured to the drainage adaptor body 152, thereby sealing the collection bag 142 and frames 148 and 150 within an interior compartment of the drainage adaptor 104 prior to use.

FIGS. 38-41 show the catheter pack 102 being moved into cooperative engagement with the drainage adaptor 104. In particular, the catheter pack 102 is oriented with the underside of the catheter pack 102 facing the upper frame 148 of the drainage adaptor 104. The underside of the catheter pack 102 is pressed against the drainage adaptor 104 to seat the upper frame 148 against or around the bottom wall 130 of the catheter pack 102. One or both of the catheter pack 102 and the drainage adaptor 104 may include clips or the like to allow the drainage adaptor 104 to be temporarily or permanently secured to the catheter pack 102. With the catheter pack 102 secured to the drainage adaptor 104, the catheter pack 102 may be rotated with respect to the drainage adaptor 104 to move it from an unaligned condition or position (FIG. 39) to a properly aligned and oriented condition or position (FIGS. 40 and 41) for use as a urinary catheter deployment cassette or system 100.

Figure 42:
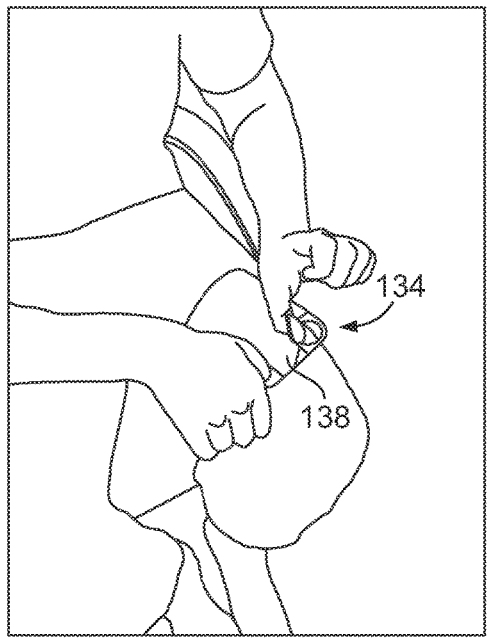
FIG. 42 illustrates a user removing the cover or lid from the packaged catheter pack of FIG. 27.
Figure 43:
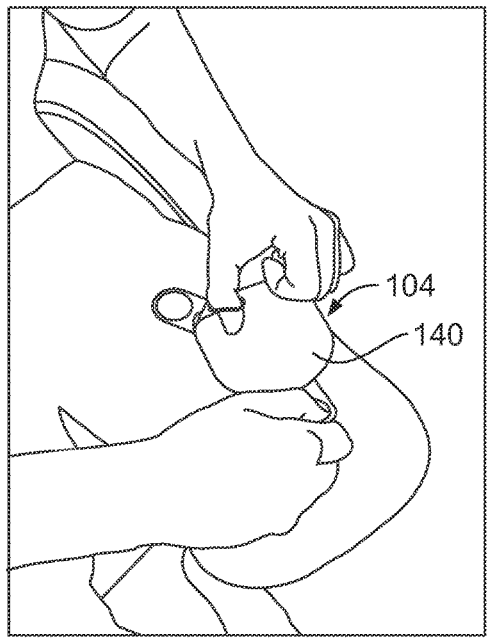
FIG. 43 illustrates a user removing the cover or lid from the packaged drainage adaptor of FIG. 28.
Figure 44:
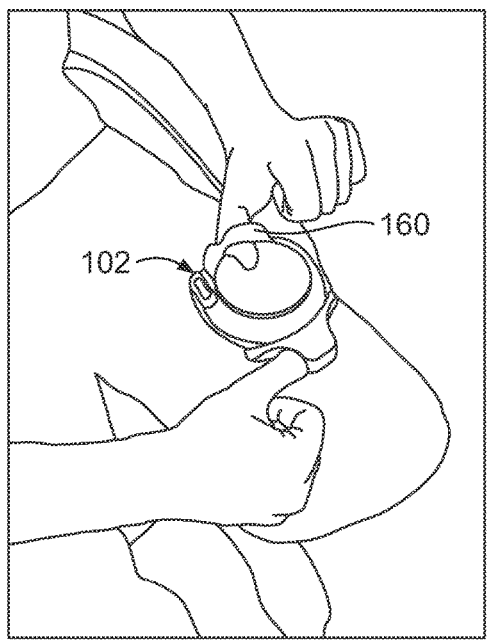
FIG. 44 illustrates a user removing a sanitary cover from the catheter pack of FIG. 42.

FIGS. 42-53 show an exemplary method of using the urinary catheter deployment cassette or system 100. First, a user obtains a catheter pack 102 and a drainage adaptor 104 and at least partially detaches or unseals the associated covers/lids (FIGS. 42-43). The covers or lids may include features or formations (e.g., the thumb holes or loops 156 of the illustrated embodiment) to facilitate gripping and removing the covers/lids for users having limited hand dexterity. If provided, the loops 156 or a separate loop or hanger or formation 158 (FIG. 29) may be used to hang the container 134 during and/or prior to use of the catheter pack 102. If the catheter pack 102 and/or drainage adaptor 104 includes an additional sanitary cover or seal 160 (e.g., a material layer overlaying the rotatable element 108, as shown in FIG. 44), it may be removed or detached at this time.

Figure 45:
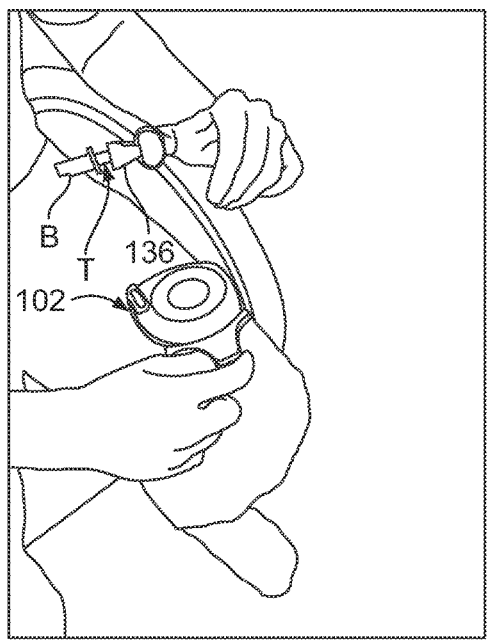
FIG. 45 illustrates a user inserting a protective tip into the catheter pack of FIG. 44.
Figure 46:
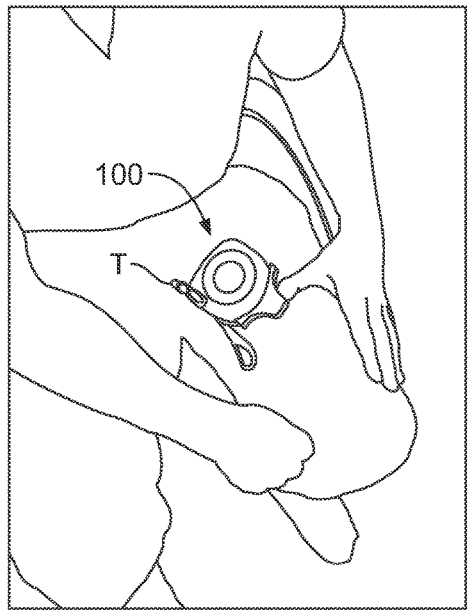
FIG. 46 illustrates a user removing a cap from the protective tip of FIG. 45.
Figure 47:
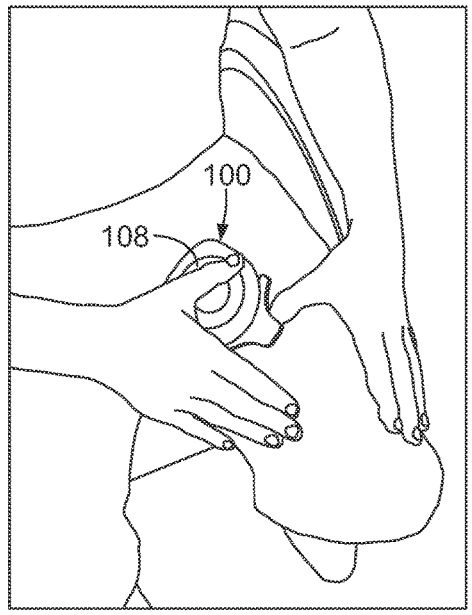
FIG. 47 illustrates a user advancing a catheter out of the catheter pack of FIG. 46 using a rotatable element of the catheter pack.
Figure 48:
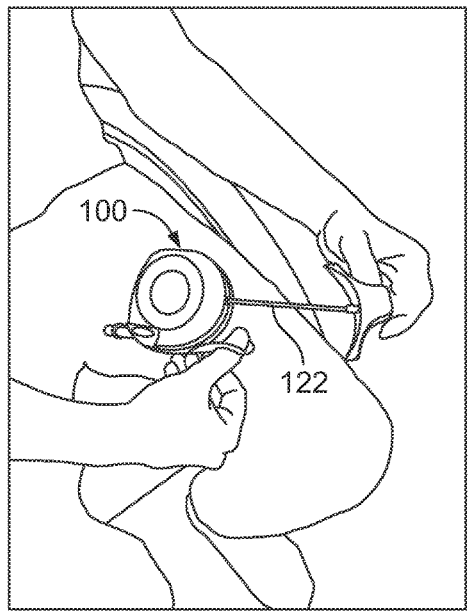
FIG. 48 illustrates a user advancing a catheter out of the catheter pack of FIG. 46 using a draw string of the catheter pack.

The user then presses the body portion B of the protective tip T into the second opening 132 of the catheter pack 102 using the cap 136, as shown in FIG. 45. The cap 136 is removed from the protective tip T, leaving the protective tip T in the second opening 132 of the catheter pack 102, as shown in FIG. 46. This may be done before or after the catheter pack 102 and the drainage adaptor 104 are pressed together and rotated into alignment to define in combination the urinary catheter deployment cassette or system 100, as described above in greater detail and shown in FIGS. 39-41.

With the urinary catheter deployment cassette or system 100 fully assembled, the user places the protective tip T of the catheter C into the urethra and then rotates the rotatable element 108 either by direct contact (FIG. 47) or using the pull string 122 (FIG. 48) to advance the catheter C, as described above. In one embodiment, the rotatable element 108 may initially be turned via direct contact to slowly advance the catheter C out of the catheter pack 102 via the second opening 132 and into the protective tip T. The protective tip T may be advanced into the urethra either prior to advancing the proximal end P of the catheter C into the protective tip T or after the proximal end P of the catheter C has been advanced into the protective tip T. In this embodiment, after the proximal end P of the catheter C has exited the protective tip T and entered the urethra, the pull string 122 of the catheter pack 102 may be pulled to more quickly advance the catheter C through the urethra until the proximal end P is properly positioned within the bladder.

Figure 49:
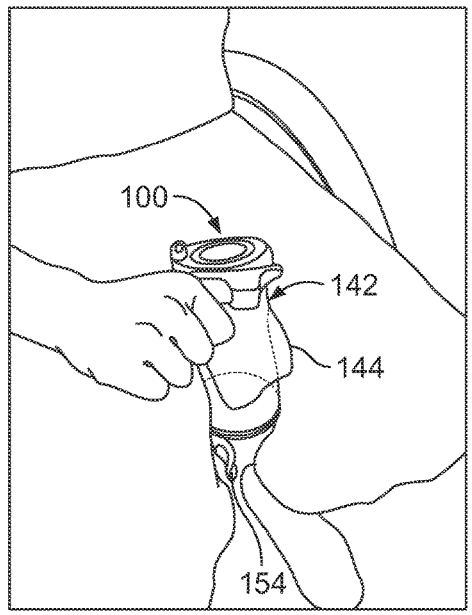
FIG. 49 illustrates a user deploying a collection bag of the drainage adaptor of FIG. 43.

With the catheter C properly positioned (or prior to the proximal end P of the catheter C being advanced into the bladder), the user may deploy and expand the collection bag 142, as shown in FIG. 49. Urine drains from the bladder into the collection bag 142 via the catheter C, with urine in the catheter C passing through the interior compartment 112 and lower opening 128 of the catheter pack 102 to reach the collection bag 142.

When the user is done with the urinary catheter deployment cassette or system 100, the catheter C is retracted from the urethra into the catheter pack 102 by rotating the rotatable element 108 in the opposite direction of the direction in which it was initially rotated to advance or pay out the catheter C. Alternatively, the catheter C may be removed from the urethra by moving the urinary catheter deployment cassette or system 100 in a distal direction away from the urethra. If provided, the strap or handle 144 of the collection bag 142 may be used to grip and move the urinary catheter deployment cassette or system 100 after use.

Figure 50:
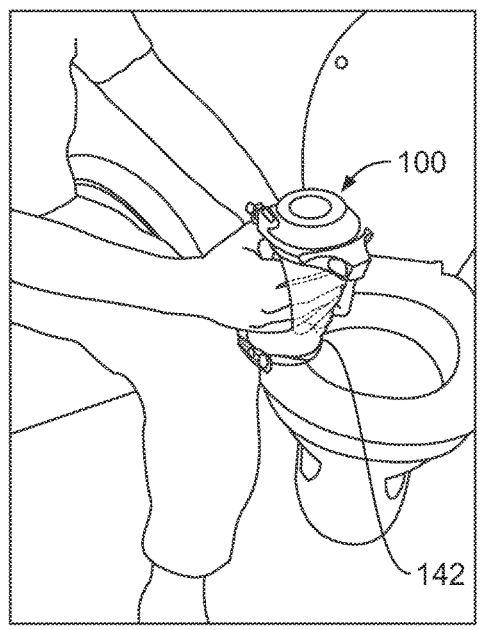
FIG. 50 illustrates a user securing the deployment system of FIGS. 46-49 to a toilet.
Figure 51:
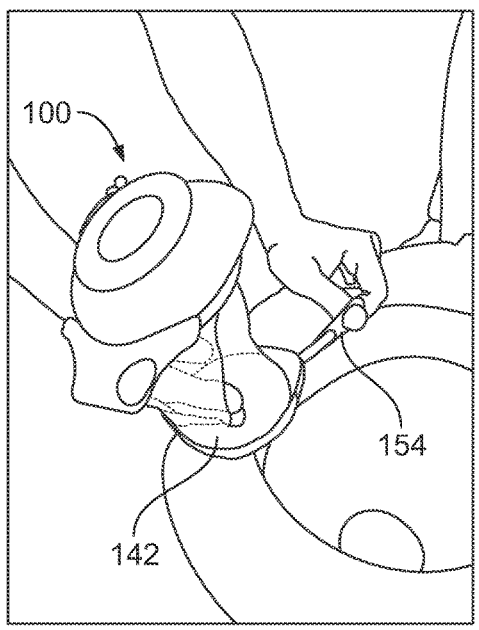
FIG. 51 illustrates a user draining urine from the deployment system of FIG. 50 into a toilet.
Figure 52:
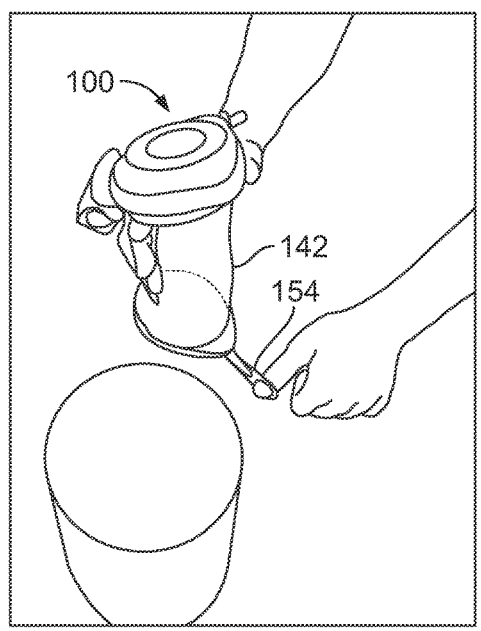
FIG. 52 illustrates a user disposing of the drainage adaptor of the deployment system of FIG. 50, after use of the deployment system.
Figure 53:
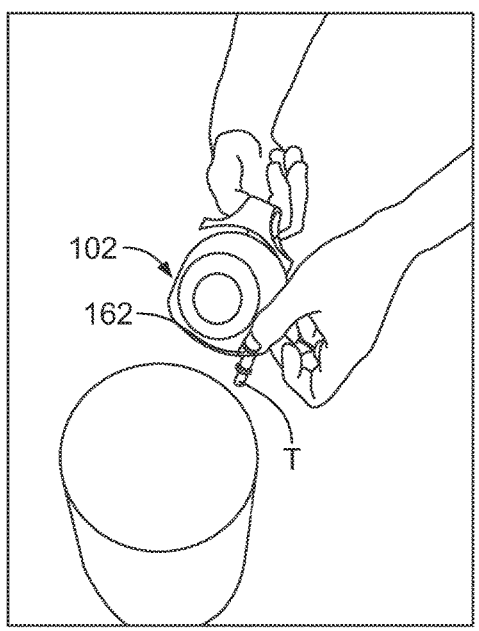
FIG. 53 illustrates a user disposing of the protective tip of the deployment system of FIG. 50, after use of the deployment system.
Figure 54:
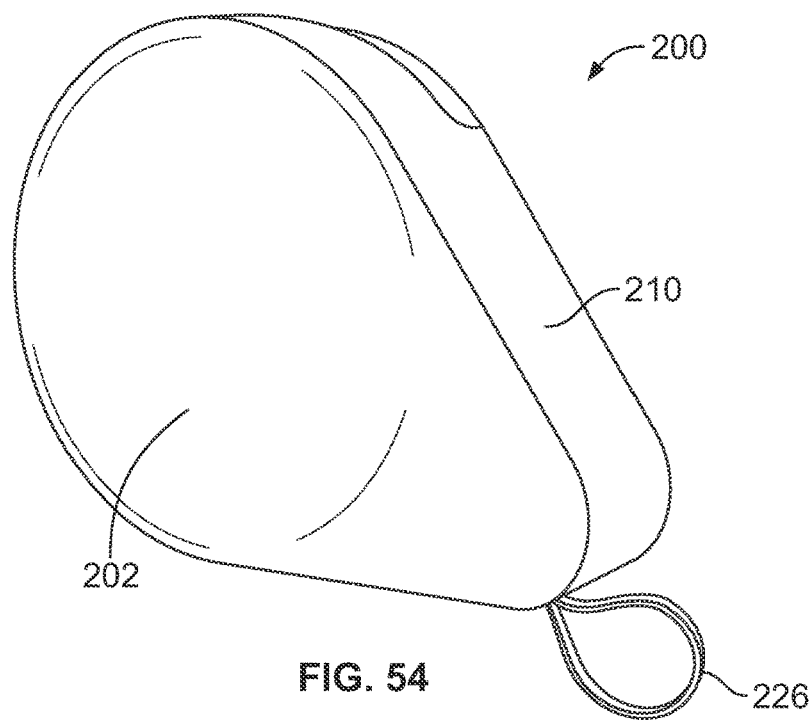
FIG. 54 is a perspective view of a urinary catheter deployment system or cassette according to another aspect of the present disclosure.

The urinary catheter deployment cassette or system 100 may then be placed adjacent to a toilet or other disposal device. If provided, the engagement feature 146 of the drainage adaptor 104 may be used to secure the collection bag 142 in place against the toilet, disposal device, or another suitable surface, as shown in FIG. 50. With the collection bag 142 in place, the pull tab 154 of the drainage adaptor 104 may be manipulated (FIG. 51) to open a portion of the collection bag 142 or a fluid passage defined in the body 152 of the drainage adaptor 104 and allow for urine to drain out of the collection bag 142 and into the toilet or disposal device.

Finally, the drainage adaptor 104 may be disposed of (FIG. 52), while the catheter pack 102 is retained for subsequent use with another drainage adaptor 104 (if the drainage adaptor 104 is disposable and the catheter pack 102 is reusable, as in a preferred embodiment). At the same time, the protective tip T may be disposed of (FIG. 53) by disassociating it from the catheter pack 102, such as by pressing an ejection or release button 162 (FIG. 31) associated with the second opening 132 of the catheter pack 102 or otherwise disconnecting the protective tip T from the catheter pack 102. The catheter pack 102 and its catheter C may be washed or otherwise decontaminated and returned to its container 134 prior to use with another drainage adaptor 104 and protective tip T.

Figure 55:
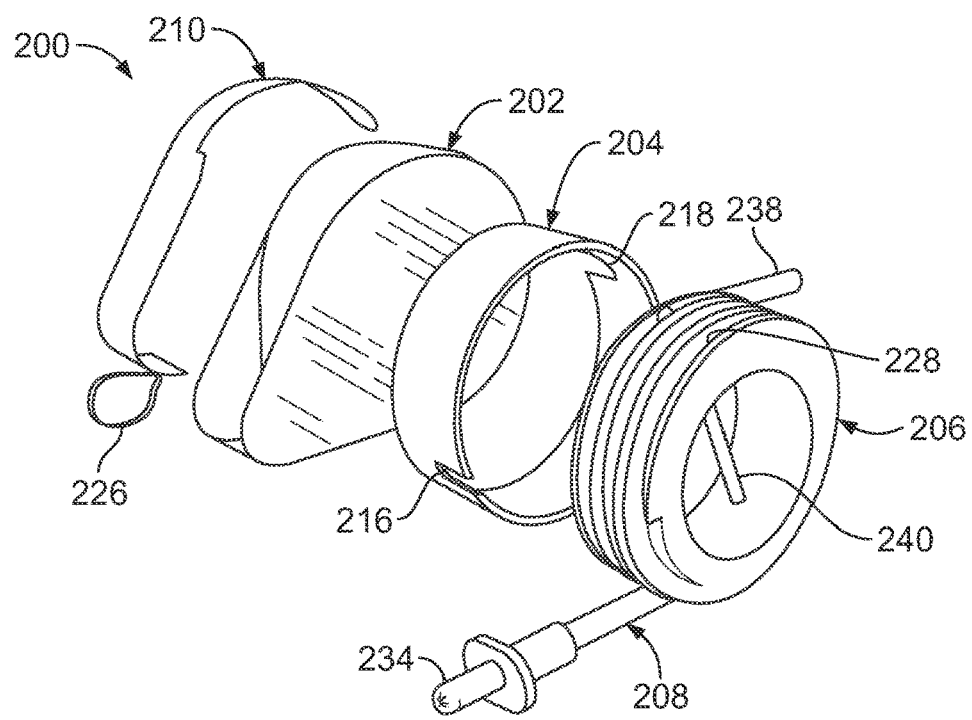
FIG. 55 is an exploded view of the system of FIG. 54.

FIGS. 54-59 illustrate another embodiment of a urinary catheter deployment cassette or system 200 (FIG. 54) according to an aspect of the present disclosure. FIG. 55 shows the various components of the system 200, which may include a body or housing 202, an outer drum 204, an inner drum 206 including a catheter 208, and a cover or lid 210. As will be described in greater detail, the system 200 may include additional or alternative components without departing from the scope of the present disclosure. For example, a permeable layer and vapor disk or sachet of the type described above with respect to the embodiment of FIGS. 4-26 may be positioned within the housing 202 to hydrate the catheter 208. In another embodiment, the outer surface of the housing 202 may include an engagement feature (e.g., an adhesive material with a removable cover, similar to the engagement feature 146 described above) to allow the housing 202 to be temporarily secured to a toilet, disposal device, or another suitable surface (such as a leg of the user) during use.

Figure 56:
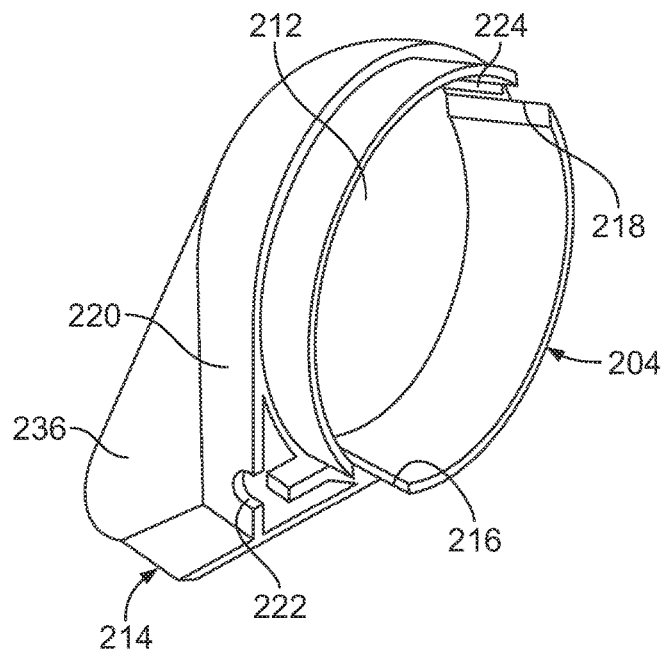
FIG. 56 is a perspective view of a housing piece and outer drum of the system of FIG. 54.

The housing 202 may be formed of a generally rigid material (e.g., a plastic material) that defines an interior compartment 212 in which the outer and inner drums 204 and 206 are at least partially received. The outer and inner drums 204 and 206 may be formed of the same material as each other and as the housing 202 or they may be formed of different material(s). The housing 202 may be formed of two separate halves or pieces, with FIG. 56 showing one of the pieces 214 of the housing 202. The other half or piece may be provided as a general mirror image of the piece 214 of FIG. 56 or may be differently configured. If multiple housing pieces are provided, they may be joined together by a snap-fit or by a weld or adhesive or mechanical fasteners or any other suitable joinder means.

At least a portion of the interior compartment 212 of the housing 202 is sized and configured to receive and immobilize the outer drum 204 (FIG. 56). The outer drum 204 may be immobilized via a friction fit or interference fit or by any other suitable means (e.g., an adhesive or mechanical fastener). It may be advantageous for the shape of the compartment 212 and housing 202 to match the shape of the outer surface of the outer drum 204 (substantially circular in the illustrated embodiment), which allows the size of the housing 202 to be decreased, making it easier for a user to discretely carry the system 200. In other embodiments, the outer surface of the outer drum 204 may be differently shaped (i.e., non-circular and non-cylindrical), with the compartment 212 and the housing 202 being adapted to either match the shape of the outer drum 204 or to be differently shaped. Regardless of the shape of the outer surface of the outer drum 204, it is preferred for the inner surface of the outer drum 204 to define a substantially circular cavity for receiving the inner drum 206, as will be described in greater detail herein.

The outer drum 204 defines at least two slots 216 and 218 that receive portions of the catheter 208 and through which the catheter 208 may pass, as will be described in greater detail. The sidewall 220 of the housing 202 (which extends generally perpendicularly between two opposing faces of the housing 202 in the illustrated embodiment) may define two openings or apertures 222 and 224 (FIG. 56), with each opening 222, 224 being aligned with a respective slot 216, 218 of the outer drum 204.

The cover or lid 210 is removably secured to the housing 202 to overlay the openings 222 and 224 of the sidewall 220, thereby isolating the interior compartment 212 from the outside environment prior to use of the system 200. The cover or lid 210 may be configured to be permanently removed from the housing 202 immediately prior to use of the system 200 or to be removed for use and then reattached afterward. If the cover or lid 210 is intended for permanent removal, it may be preferred for it to be formed of a foil material or the like that is sealed to the sidewall 220 of the housing 202 to overlay at least the openings 222 and 224. If the cover or lid 210 is intended for removal and then reattachment, it may be formed of a more durable material, such as plastic or the like, that is snap- or friction-fit onto the housing 202 or attached by any other suitable means. The cover or lid 210 may include a formation that simplifies removal of the cover or lid 210, such as the illustrated thumb loop or tab 226. Additionally, while the illustrated embodiment includes only a single cover or lid 210, it is within the scope of the present disclosure for the system 200 to include multiple covers of lids, such as a separate cover or lid associated and overlaying each of the openings 222 and 224 of the sidewall 220.

Figure 57:
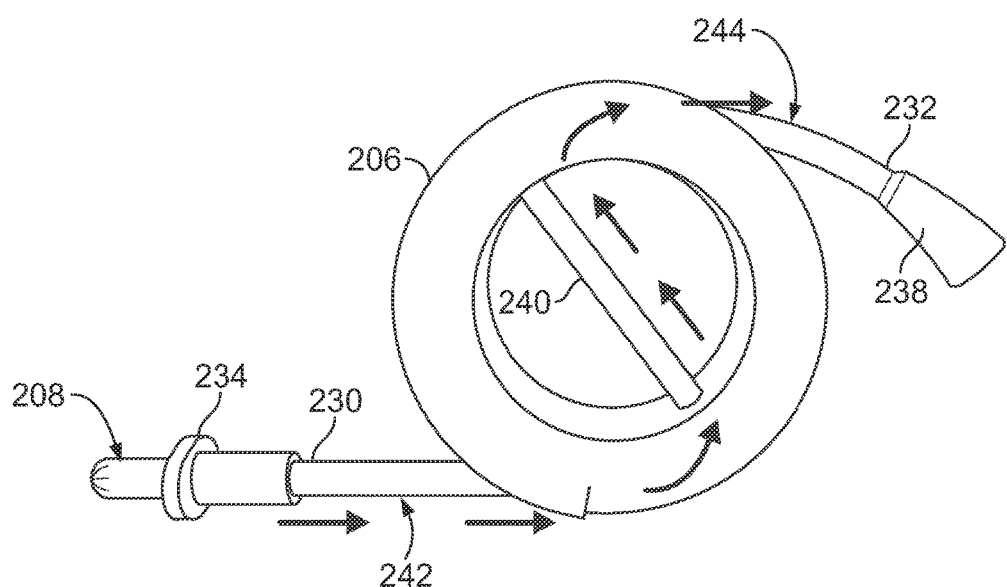
FIG. 57 is a side elevational view of an inner drum and catheter of the system of FIG. 54.

The inner drum 206 and associated catheter 208 are illustrated in greater detail in FIG. 57. The illustrated inner drum 206 is generally annular or cylindrical, with an outer diameter that is no greater than the inner diameter of the associated outer drum 204. By such a configuration, the inner drum 206 may be positioned concentrically within the outer drum 204 (FIG. 58), with the catheter 208 (which extends beyond the outer perimeter of the inner drum 206) positioned within the slots 216 and 218 of the outer drum 206. Preferably, the outer diameter of the inner drum 206 is substantially the same as the inner diameter of the outer drum 204, such that the inner drum 206 is positioned inwardly of the outer drum 204 without allowing translational movement of the inner drum 206 with respect to the outer drum 204. While it is advantageous to avoid relative translational movement, the inner drum 206 is configured to rotate with respect to the outer drum 204 and the housing 202, as will be described in greater detail.

The outer surface or perimeter of the inner drum 206 includes one or more grooves 228 (FIG. 55) in which a portion of the catheter 208 between the proximal end 230 and the distal end 232 may be positioned. Preferably, the depth of the groove or grooves 228 is at least equal to the diameter of the portion of the catheter 208 positioned therein to allow the catheter 208 to be positioned fully within the groove or grooves 228 without extending beyond the perimeter of the inner drum 206. The outer drum 204 serves to ensure that the catheter 208 remains within the groove or grooves 228, rather than uncoiling or deforming to be positioned outside of the groove or grooves 228. In another embodiment, the outer drum 204 may be omitted, with the compartment 212 being shaped and configured to provide the same function that is provided by the outer drum 204, although the use of an outer drum 204 may be preferred to simplify manufacturing and assembly of the system 200.

Figure 58:
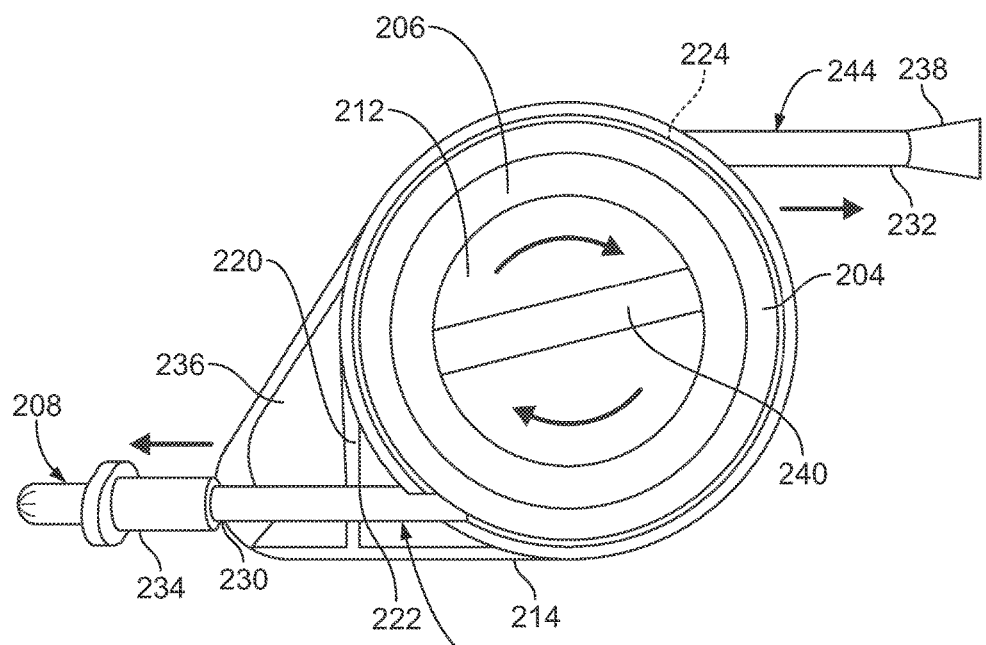
FIG. 58 is a side elevational view of the system of FIG. 54, with a housing piece and cover or lid omitted for illustrative purposes.
Figure 59:
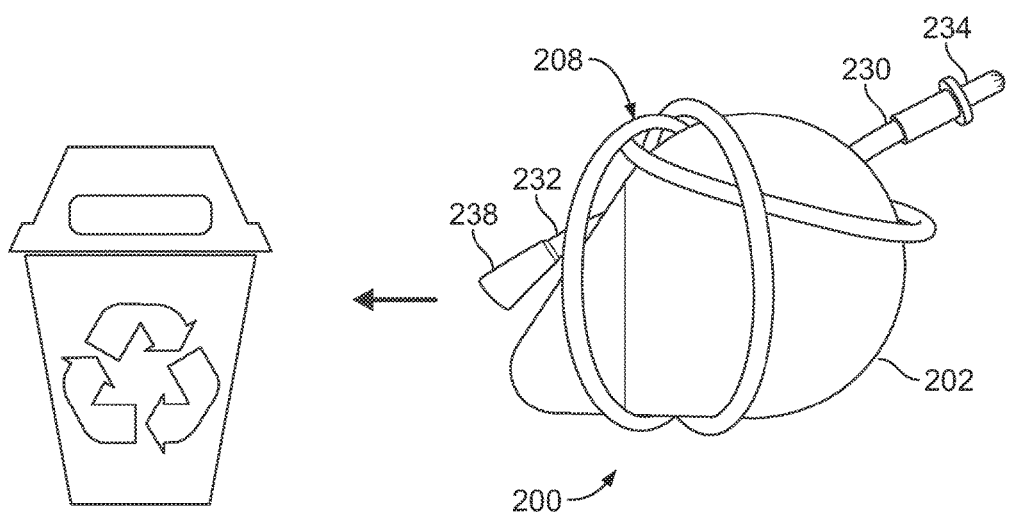
FIG. 59 is a side elevational view of the system of FIG. 54, with the catheter wrapped around the housing for disposal following use.

The proximal end 230 of the catheter 208 may include a protective tip 234 having a greater diameter than the groove or grooves 228, such that the protective tip 234 is positioned outside of the groove or grooves 228 and the inner drum 206, as shown in FIGS. 55, 57, and 58. In this case, the housing 202 may be configured to accommodate the protruding protective tip 234, such as by having an overall non-circular shape (e.g., a teardrop-shape, as in FIG. 54), although it is also within the scope of the present disclosure for the housing 202 to be generally circular. In the illustrated embodiment, the housing 202 includes a second chamber or compartment 236 that is separated from the first compartment 212 by the sidewall 220, with one of the openings 222 communicating between the compartments 212 and 236. The catheter 208 passes through the opening 222 (and the associated slot 216 of the outer drum 204), with the protective tip 234 and proximal end 230 of the catheter 208 positioned within the second compartment 236 and the remainder of the catheter 208 positioned within the first compartment 212 (along with the outer and inner drums 204 and 206). The protective tip 234 preferably has a diameter greater than the opening 222 to prevent the protective tip 234 from moving from the second compartment 236 into the first compartment 212 via the opening 222.

Similar to the protective tip 234, at least a portion of the connecting member or funnel 238 of the catheter 208 may be positioned outside of the groove or grooves 228 of the inner drum 206, as shown in FIG. 55. In the illustrated embodiment, the funnel 238 is positioned within the same compartment 212 as the outer and inner drums 204 and 206 (unlike the protective tip 234), but it is also within the scope of the present disclosure for the housing 202 to define an additional compartment (separated from the first compartment 212 by the sidewall 220, for example) in which the funnel 238 or a portion thereof may be positioned prior to use. The funnel 238 and/or a portion of the distal end 232 of the catheter 208 extends through one of the slots 218 in the outer drum 204, which is aligned with one of the openings 224 in the housing sidewall 220, as described above.

In the illustrated embodiment, a tubular extension or joining tube 240 extends across the open interior of the inner drum 206, from one location of the inner surface of the inner drum 206 to another location. The joining tube 240 may be formed of a generally flexible material or a generally rigid material or a material having an intermediate rigidity. The joining tube 240 is shown as extending through the central axis about which the inner drum 206 is defined (i.e., along a diameter), but it is also within the scope of the present disclosure for the joining tube 240 (if provided) to extend between one location of the inner surface of the inner drum 206 to a second location that is not diametrically spaced from the first location.

When a joining tube 240 is provided, the catheter 208 may be provided in two separate pieces 242 and 244, with a proximal piece 242 that includes the proximal end 230 and a distal piece 244 that includes the distal end 232. The two pieces 242 and 244 of the catheter 208 are provided in fluid communication with the opposite ends of the joining tube 240, such that the two catheter pieces 242 and 244 are in fluid communication with each other through the joining tube 240. The inner drum 206 may include an opening or aperture at the locations where the joining tube 240 meets the inner drum 206, with each catheter piece 242, 244 being associated with one of the openings or apertures by a fluid-tight connection. By such a configuration, urine flows into the proximal catheter piece 242, through the joining tube 240, and then into the distal catheter piece 244 (FIG. 57), where it may be drained from the system 200 (as will be described in greater detail herein). While the embodiment of FIGS. 54-59 is provided with a joining tube 240 and a two-piece catheter 208, it is within the scope of the present disclosure for the joining tube 240 to be omitted and for the two-piece catheter 208 to be replaced by a one-piece catheter that is wound around the inner drum 206.

The inner drum 206 is configured to rotate within the cavity defined by the inner surface of the outer drum 204, with rotation of the inner drum 206 about its central axis in a particular direction (in a clockwise direction in the orientation of FIGS. 57 and 58) causing the ends 230 and 232 of the catheter 208 to be advanced out of the openings 222 and 224 in the housing sidewall 220. Similarly, grasping and pulling one of the ends 230, 232 of the catheter 208 out of the housing 202 will cause the inner drum 206 to rotate and the other end 232, 230 of the catheter 208 to be advanced out of the housing 202. For example, according to one method of using the system 200, a user positions the protective tip 234 within the urethra and then pulls the funnel 238 distally away from the housing 202, which has the effect of rotating the inner drum 206 and advancing the proximal end 230 of the catheter 208 through the urethra until it reaches the bladder. Urine drains from the bladder, through the catheter 208 (including the portion of the catheter 208 positioned within the housing 202), and then out of the catheter 208 via the funnel 238, which may direct the urine into a toilet or the like. Thereafter, the housing 202 may be moved away from the body to retract the proximal end 230 of the catheter 208 from the urethra. With the catheter 208 fully removed from the urethra, it may be wrapped around the housing 202 (optionally being tied into a simple knot to retain the system 200 in a compact configuration) for disposal into a waste container (FIG. 59), such as a garbage can. If the system 200 is made of recyclable materials, then it may be placed into a recycling bin or container instead of a garbage can.

In another embodiment, it is possible to retract the catheter 208 into the housing 202 after use. In such an embodiment, a separate introducer aid of the type described above with respect to the embodiment of FIGS. 4-26 may be employed. In such an embodiment, the housing 202 may be configured to allow the introducer aid to engage the inner drum 206 or a portion thereof (e.g., the joining tube 240, especially if it is formed of a generally rigid material). This may be accomplished by providing a deformable or pierceable housing wall or section, as in the embodiment of FIGS. 4-26, with the introducer aid being pressed against the housing 202 to bring an engagement member of the introducer aid into engagement with the inner drum 206 or a portion thereof. With the introducer aid and housing 202 so connected, a rotatable element of the introducer aid (such as a disk of the type described above with respect to the embodiment of FIGS. 4-26) may be rotated to rotate the engagement member, which rotates the inner drum 206 to advance the catheter 208 out of the housing 202. After use, the rotatable element may be rotated in the opposite direction to retract the catheter 208 into the housing 202 for disposal or cleaning and reuse. Other means and methods for retracting the catheter 208 into the housing 202 after use may also be employed without departing from the scope of the present disclosure.

It should be understood that the methods described herein are merely exemplary, and that the steps described above may be carried out in a different order. Further, other steps may be included when using the devices described herein. Additionally, one or more of the steps described herein in connection with the methods may be omitted or modified without departing from the scope of the present disclosure. Similarly, the systems described herein are merely exemplary, and they may be differently configured (e.g., by combining one or more components of one described embodiment with one or more components of another described embodiment) without departing from the scope of the present disclosure.

Aspects of the present subject matter described above may be beneficial alone or in combination with one or more other aspects. Without limiting the foregoing description, in accordance with one aspect of the subject matter herein, there is provided a urinary catheter deployment system, which includes a catheter pack and an introducer aid. The catheter pack defines an interior compartment in which a rotatable spindle and urinary catheter are at least partially positioned. A deformable or pierceable cover is associated with the interior compartment. The introducer aid includes at least one spindle engagement member configured to cooperate with the catheter pack to deform or pierce the cover and engage the spindle for deploying the urinary catheter from the catheter pack.

In accordance with another aspect which may be used or combined with the first aspect, the spindle includes a chamber in fluid communication with the urinary catheter for receiving fluid passing through the urinary catheter.

In accordance with another aspect which may be used or combined with the second aspect, a drainage channel is associated with the chamber of the spindle for draining fluid in the chamber from the catheter pack.

In accordance with another aspect which may be used or combined with the third aspect, the drainage channel is movable between a retracted position and an extended position, with a greater portion of the drainage channel being positioned within the chamber of the spindle when the drainage channel is in the retracted position than when the drainage channel is in the extended position.

In accordance with another aspect which may be used or combined with the any of the preceding aspects, the spindle includes a cavity configured to receive at least a portion of the spindle engagement member.

In accordance with another aspect which may be used or combined with the fifth aspect, the cavity has a shape complementary to the shape of the portion of the spindle engagement member that is received by the cavity.

In accordance with another aspect which may be used or combined with any of the preceding aspects, the introducer aid includes a rotatable element and a pull string configured to separately rotate the spindle engagement member.

In accordance with another aspect, there is provided a urinary catheter deployment system including a catheter pack defining an interior compartment. A rotatable spindle and urinary catheter are at least partially positioned within the interior compartment of the catheter pack. A pusher is also at least partially positioned within the interior compartment of the catheter pack and is associated with the spindle. The pusher is configured to rotate with the spindle and contact the urinary catheter, thereby deploying the urinary catheter from the catheter pack.

In accordance with another aspect which may be used or combined with the preceding aspect, a protective tip is configured to receive at least a portion of the urinary catheter. The catheter pack includes an upper opening from which the urinary catheter is deployed, with the upper opening receiving at least a portion of the protective tip and orienting the protective tip such that at least a portion of the urinary catheter is advanced into the protective tip during deployment of the urinary catheter from the catheter pack.

In accordance with another aspect which may be used or combined with the preceding aspect, the catheter pack includes a release button configured to be pressed to dissociate the protective tip from the upper opening.

In accordance with another aspect which may be used or combined with any of the preceding three aspects, a generally helical track is at least partially positioned within the interior compartment of the catheter pack, with at least a portion of the urinary catheter being positioned within the track.

In accordance with another aspect which may be used or combined with any of the preceding four aspects, a drainage adaptor is configured to be placed into fluid communication with the interior compartment of the catheter pack for transferring fluid from the interior compartment of the catheter pack and/or the urinary catheter to the drainage adaptor.

In accordance with another aspect which may be used or combined with the preceding aspect, the drainage adaptor includes a collapsible collection bag configured to receive fluid from the interior compartment of the catheter pack and/or the urinary catheter.

In accordance with another aspect which may be used or combined with any of the preceding two aspects, the drainage adaptor includes a pull tab configured to be actuated to drain fluid from the drainage adaptor.

In accordance with another aspect which may be used or combined with any of the preceding seven aspects, the catheter pack includes a rotatable element and a pull string configured to separately rotate the spindle.

In accordance with another aspect which may be used or combined with any of the preceding aspects, the urinary catheter is a hydrophilic urinary catheter. A vapor-donating fluid is positioned within the interior compartment of the catheter pack and emits a vapor that contacts at least a portion of the urinary catheter.

In accordance with another aspect, there is provided a urinary catheter deployment system including a housing defining an interior compartment. A rotatable inner drum and a urinary catheter are at least partially positioned within the interior compartment of the catheter pack. The urinary catheter is associated with the inner drum such that rotation of the inner drum deploys the urinary catheter from the housing. The urinary catheter includes separate first and second pieces that are secured to the inner drum. The inner drum includes a joining tube in fluid communication with the first and second pieces of the urinary catheter.

In accordance with another aspect which may be used or combined with the preceding aspect, an outer surface of the inner drum includes at least one groove and at least a portion of the urinary catheter is positioned within the at least one groove.

In accordance with another aspect which may be used or combined with any of the preceding two aspects, an outer drum is at least partially positioned within the interior compartment of the housing. The outer drum is configured to be substantially stationary with respect to the housing, encircles the inner drum, and includes at least two slots through which the urinary catheter extends.

In accordance with another aspect which may be used or combined with any of the preceding three aspects, the housing defines at least two openings and rotation of the inner drum causes the first piece of the urinary catheter to be deployed from the housing via one of the openings of the housing and the second piece of the urinary catheter to be deployed from another one of the openings of the housing.

In accordance with another aspect which may be used or combined with any of the preceding four aspects, the urinary catheter includes a proximal end and a protective tip associated with the proximal end. The housing defines a second interior compartment, with the protective tip being at least partially positioned within the second interior compartment.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A urinary catheter deployment system, comprising:
    a catheter pack defining an interior compartment and including a deformable or pierceable cover associated with the interior compartment;
    a rotatable spindle at least partially positioned within the interior compartment of the catheter pack;
    a urinary catheter at least partially positioned within the interior compartment of the catheter pack and associated with the spindle; and
    an introducer aid including at least one spindle engagement member configured to cooperate with the catheter pack to deform or pierce the cover and, upon deforming or piercing the cover, engage the spindle, wherein rotation of the at least one spindle engagement member causes rotation of the spindle for deploying the urinary catheter from the catheter pack.

2. The urinary catheter deployment system of claim 1, wherein the spindle includes a chamber in fluid communication with the urinary catheter for receiving fluid passing through the urinary catheter.

3. The urinary catheter deployment system of claim 2, further comprising a drainage channel associated with the chamber of the spindle for draining fluid in the chamber from the catheter pack.

4. The urinary catheter deployment system of claim 1, wherein the spindle includes a cavity configured to receive at least a portion of the at least one spindle engagement member.

5. The urinary catheter deployment system of claim 4, wherein the cavity has a shape complementary to the shape of the portion of the at least one spindle engagement member that is received by the cavity.

6. The urinary catheter deployment system of claim 1, wherein
    the introducer aid includes a rotatable element and a pull string,
    the rotatable element is configured to be actuated to rotate the spindle engagement member without actuation of the pull string, and
    the pull string is configured to be actuated to rotate the spindle engagement member without actuation of the rotatable element.

7. The urinary catheter deployment system of claim 1, wherein
    the catheter pack further defines a second interior compartment adjacent to and adjoining the interior compartment, and
    a portion of the urinary catheter is positioned within the second interior compartment.

8. The urinary catheter deployment system of claim 7, wherein
    at least a portion of the second interior compartment is defined by a sidewall,
    the sidewall defines a gap, and
    said portion of the urinary catheter positioned within the second interior compartment is accessible through the gap.

9. The urinary catheter deployment system of claim 8, further comprising a side cover sealed to the sidewall, covering the gap, and configured to be at least partially detached from the sidewall to allow access to the second interior compartment via the gap.

10. The urinary catheter deployment system of claim 1, further comprising a retention feature associated to an underside of the catheter pack, configured to be held by a user to stabilize and/or orient the catheter pack.

11. The urinary catheter deployment system of claim 10, wherein the retention feature is configured as a hand strap.

12. The urinary catheter deployment system of claim 1, wherein
    the introducer aid includes a rotatable element configured to rotate the spindle engagement member, and
    the rotatable element is configured to be rotated by direct contact by a user.

13. The urinary catheter deployment system of claim 12, wherein a portion of the rotatable element is textured for improved traction during rotation of the rotatable element by direct contact by a user.

14. The urinary catheter deployment system of claim 1, wherein the catheter pack and the introducer aid are configured to allow for only one orientation of the introducer aid with respect to the catheter pack when the at least one spindle engagement member is in engagement with the spindle.

15. The urinary catheter deployment system of claim 1, wherein the introducer aid is configured to be temporarily retained or locked together with the catheter pack when the at least one spindle engagement member is in engagement with the spindle.

16. The urinary catheter deployment system of claim 1, wherein
    the catheter pack includes an extending clip or rim,
    the introducer aid includes a groove or lip configured to receive the clip or rim, and
    the introducer aid is temporarily retained or locked together with the catheter pack when the clip or rim is received by the groove or lip.

17. The urinary catheter deployment system of claim 1, wherein a portion of the cover overlaying the spindle is configured to be more deformable or more pierceable than other portions of the cover.

18. The urinary catheter deployment system of claim 1, wherein a portion of the cover overlaying the spindle is the only portion of the cover configured to be deformed or pierced by the at least one spindle engagement member.

19. The urinary catheter deployment system of claim 1, wherein the introducer aid includes a removal aid configured to be gripped by a user for disengagement of the at least one spindle engagement member from the spindle.

20. A urinary catheter deployment system, comprising
    a catheter pack defining an interior compartment and including a deformable or pierceable cover associated with the interior compartment;

a rotatable spindle at least partially positioned within the interior compartment of the catheter pack;

a urinary catheter at least partially positioned within the interior compartment of the catheter pack and associated with the spindle; and an introducer aid including at least one spindle engagement member configured to cooperate with the catheter pack to deform or pierce the cover and engage the spindle for deploying the urinary catheter from the catheter pack, wherein the spindle includes a chamber in fluid communication with the urinary catheter for receiving fluid passing through the urinary catheter, a drainage channel is associated with the chamber of the spindle for draining fluid in the chamber from the catheter pack, and the drainage channel is movable between a retracted position and an extended position, with a greater portion of the drainage channel being positioned within the chamber of the spindle when the drainage channel is in the retracted position than when the drainage channel is in the extended position.

\* \* \* \* \*